United States Patent [19]

Fowler, Jr. et al.

[11] Patent Number: 5,086,776
[45] Date of Patent: Feb. 11, 1992

[54] APPARATUS AND METHOD FOR SENSING CARDIAC PERFORMANCE

[75] Inventors: Franklin S. Fowler, Jr.; Russell P. Jurgensen, both of Camano Island, Wash.

[73] Assignee: Precision Diagnostics, Inc., Stanwood, Wash.

[21] Appl. No.: 490,044

[22] Filed: Mar. 6, 1990

[51] Int. Cl.$^5$ ............................................. A61B 8/02
[52] U.S. Cl. .......................... 128/661.09; 128/661.08; 128/715
[58] Field of Search ...................... 128/661.07, 661.08, 128/661.09, 661.10, 715

[56] References Cited

U.S. PATENT DOCUMENTS

| 3,101,082 | 8/1963 | Steen et al. | 128/680 |
|---|---|---|---|
| 3,157,177 | 11/1964 | Smith et al. | 128/680 |
| 3,444,856 | 5/1969 | Settler et al. | 128/679 |
| 3,605,723 | 9/1971 | King et al. | 128/661.07 |
| 3,773,033 | 11/1973 | Rodbard et al. | 128/700 |
| 3,776,221 | 12/1973 | McIntyre | 128/672 |
| 3,881,481 | 5/1975 | Heule et al. | 128/713 |
| 3,908,639 | 9/1975 | McIntyre | 128/672 |
| 4,094,308 | 6/1978 | Cormier | 128/715 |
| 4,112,929 | 9/1978 | Affeldt et al. | 128/680 |
| 4,137,910 | 2/1979 | Murphy | 128/713 |
| 4,245,648 | 1/1981 | Trimmer et al. | 128/672 |
| 4,269,193 | 5/1982 | Eckerle | 128/672 |
| 4,289,141 | 9/1981 | Cormier | 128/713 |
| 4,446,872 | 5/1984 | Marsoner et al. | 128/715 |
| 4,450,527 | 5/1984 | Sramek | 128/670 |
| 4,548,204 | 10/1985 | Groch et al. | 128/904 |
| 4,566,462 | 1/1986 | Janssen | 128/661.07 |
| 4,572,197 | 2/1986 | Moore et al. | 128/644 |
| 4,628,939 | 12/1986 | Little et al. | 128/696 |
| 4,672,977 | 6/1987 | Kroll | 128/715 |
| 4,677,984 | 7/1987 | Sramek | 128/681 |
| 4,759,374 | 7/1988 | Kierney et al. | 128/661.09 |
| 4,799,491 | 1/1989 | Eckerle | 128/672 |
| 4,802,488 | 2/1989 | Eckerle | 128/672 |
| 4,803,996 | 2/1989 | Peel et al. | 128/710 |
| 4,807,638 | 2/1989 | Sramek | 128/672 |
| 4,905,706 | 3/1990 | Duff et al. | 128/701 |
| 4,917,115 | 4/1990 | Flammang et al. | 128/661.07 |
| 4,920,969 | 5/1990 | Suzuki et al. | 128/659 |
| 4,967,760 | 11/1990 | Bennett, Jr. et al. | 128/715 |

OTHER PUBLICATIONS

Dennis S. Miura, MD, PhDS, & Kenneth Dangman, PhD, Cardiovascular Reviews and Reports, "Noninvasive Measurement of Left Ventricular Performance", vol. 7, No. 12, Dec. 1986, pp. 1022-1028.
R. P. Lewis, R. F. Leighton, W. F. Forester, & A. M. Weissler, Noninvasive Cardiology, "Systolic Time Intervals", Chap. 6, 1973, pp. 301-368.
VERSATONE Doppler Model D8 brochure, p. 1.
IMEXLAB 3000 Applications Handbook, p. 1.
IMEXLAB 3000 Quick Reference Guide, p. 1.
IMEXLAB 3000 Vascular Diagnostics System Operations Manual, p. 1.
IMEXLAB 3000 Vascular Recorder Instructional Program tape, cover information.

Primary Examiner—Francis Jaworski
Assistant Examiner—George Manuel
Attorney, Agent, or Firm—Larry A. Jackson; John M. Johnson

[57] ABSTRACT

An apparatus and method for sensing cardiac performance by providing real time values of left ventricular performance of ambulatory or inactive subjects. Noninvasive sensors such as noise reducing phonocardiographic sensors, multi-crystal piezoelectric doppler pulse wave sensors, volume oscillometric pulse wave sensors, and electrocardiographic sensors develop a plurality of electrical signals representing certain key physiological functions. These electrical signals are uniquely conditioned and combined by a central processing unit and associated programs to yield real time outputs of Left Ventricular Ejection Time, Systolic Time Interval and Ejection Fraction for either ambulatory or inactive patients. These values are displayed, along with analog patient cardiac-based waveforms, on a recording device and may be used for future playback.

39 Claims, 22 Drawing Sheets

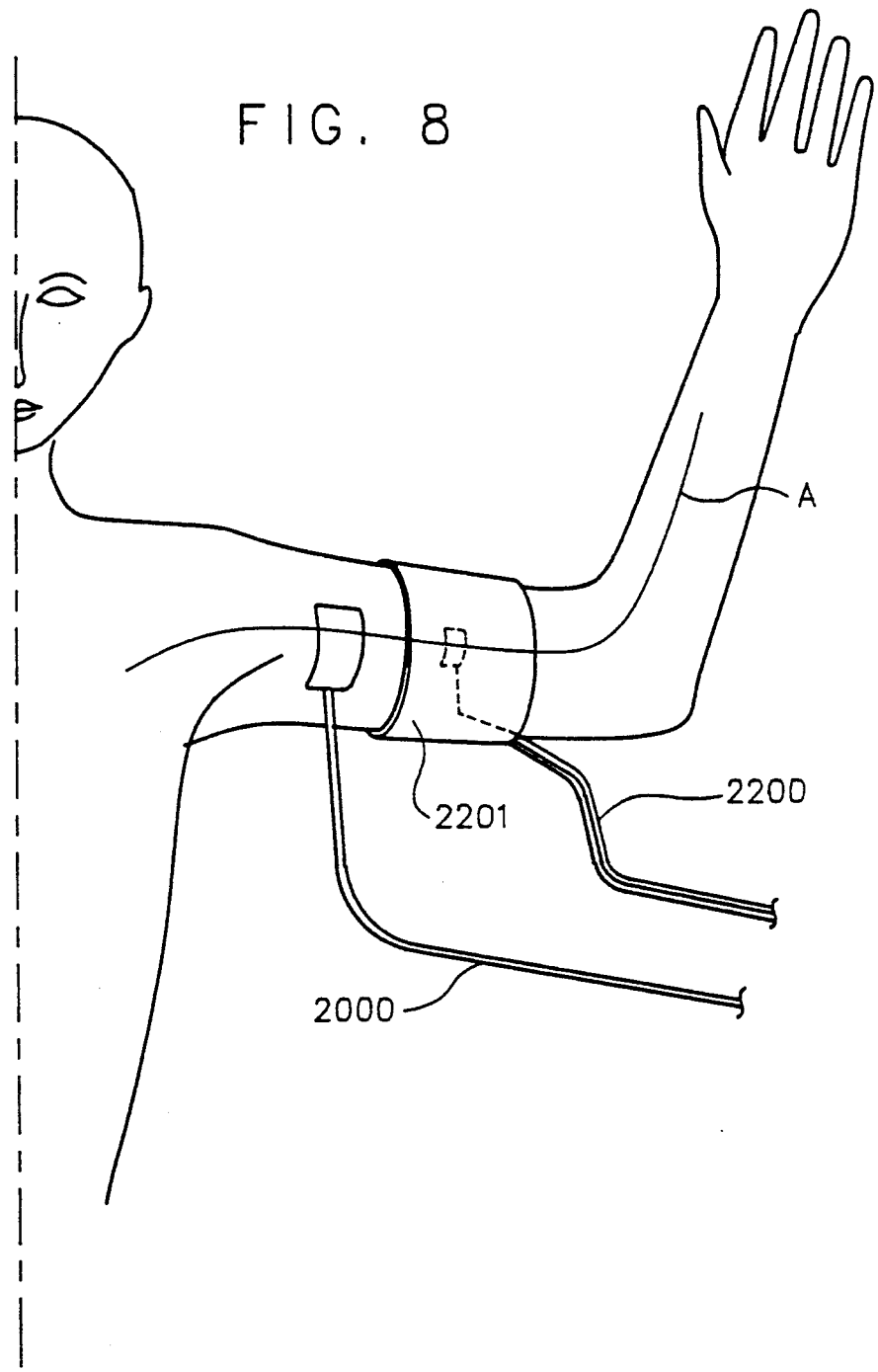

TO TRANSMIT CIRCUIT    TO RECEIVE CIRCUIT

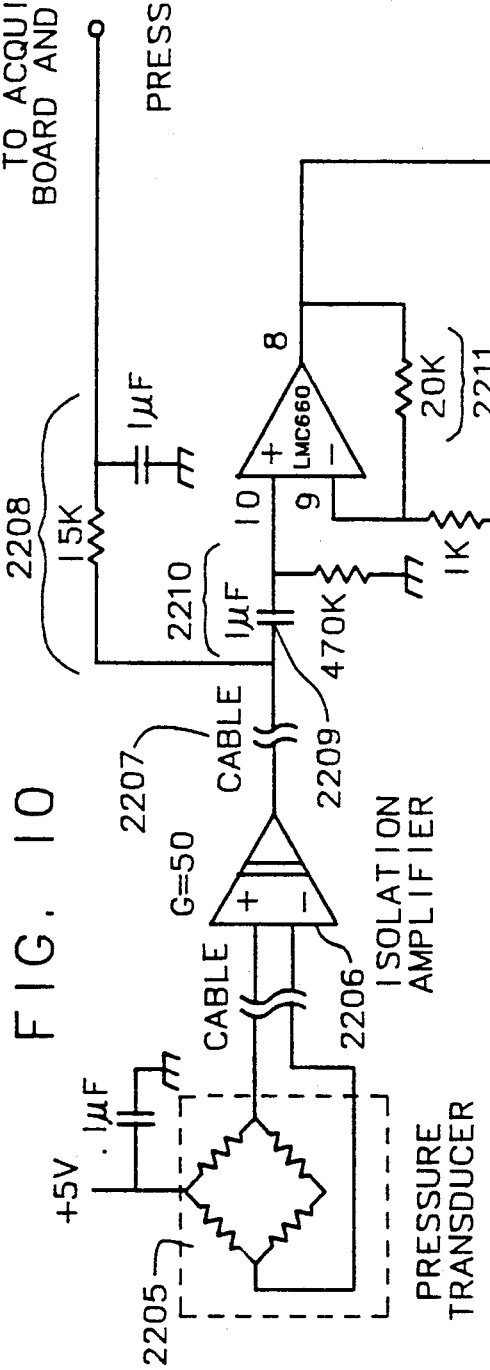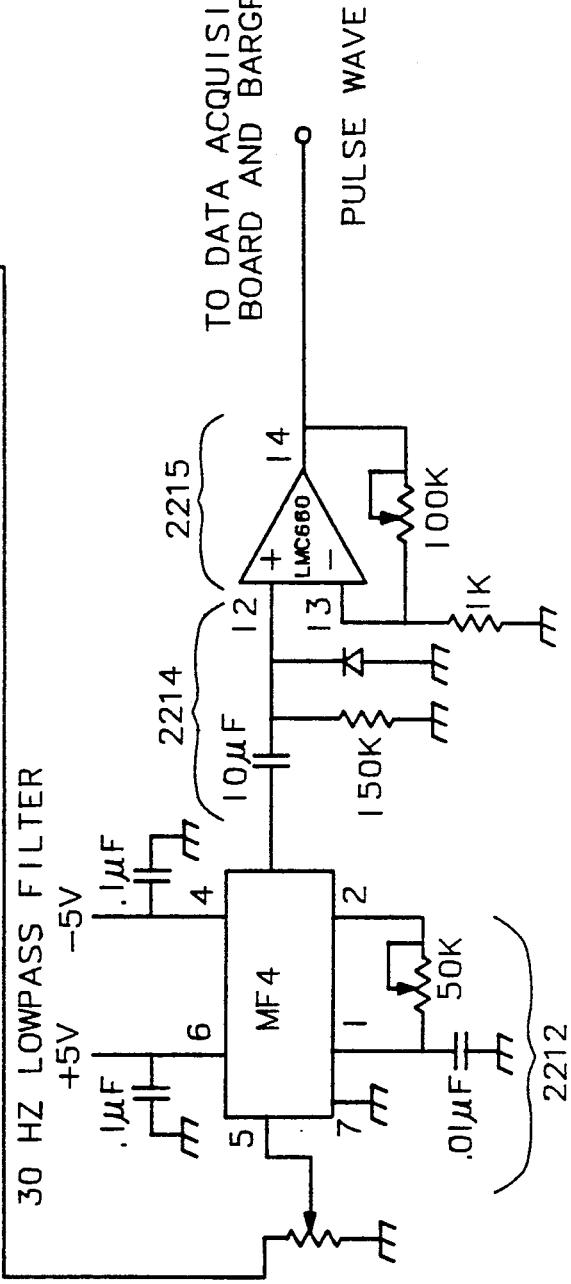
FIG. 10

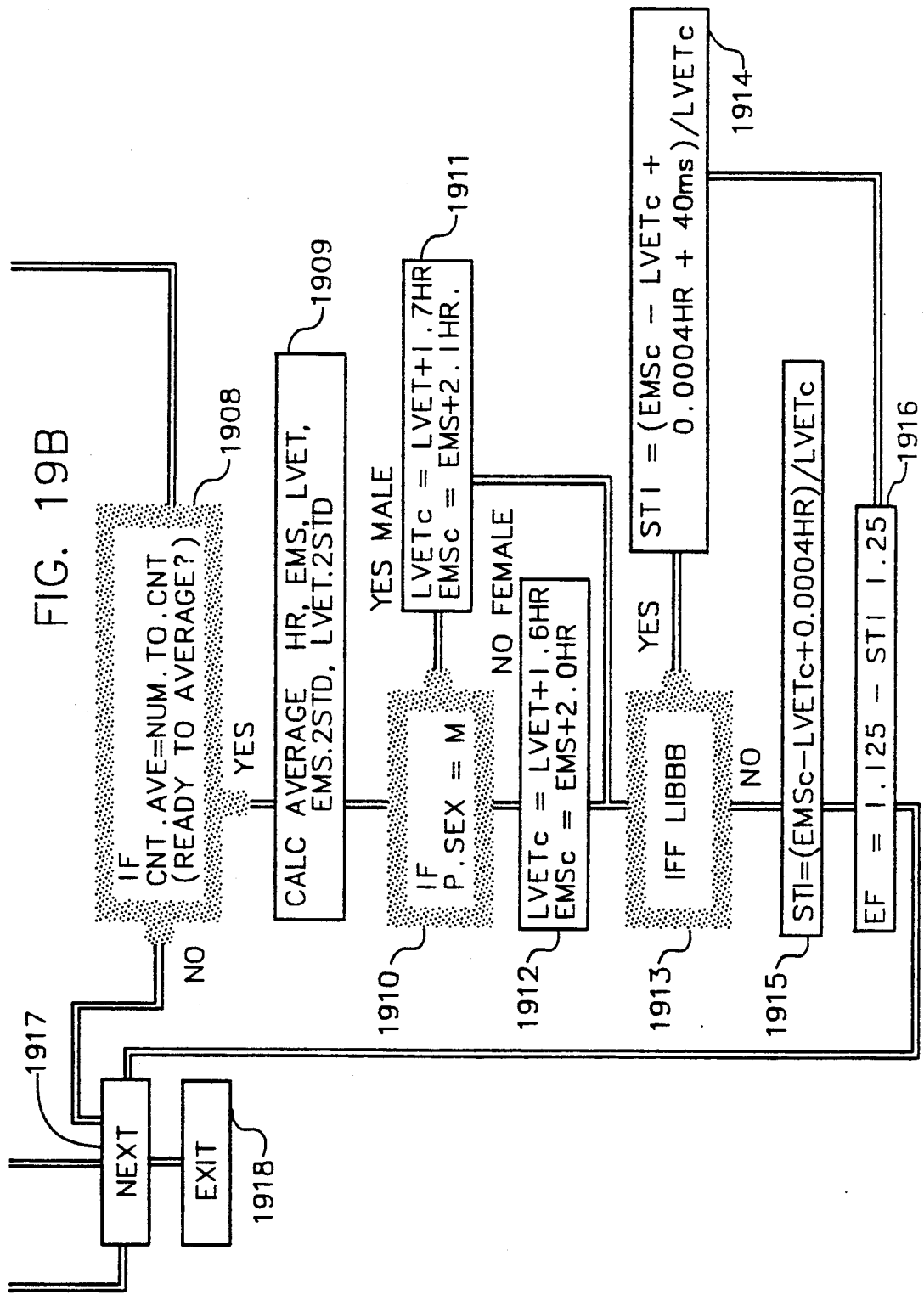

APPARATUS AND METHOD FOR SENSING CARDIAC PERFORMANCE

BACKGROUND OF THE INVENTION

This invention relates to instrumentation for measuring the performance of the heart's left ventricle. Such data has proven valuable in prognostic evaluation of cardiac cases.

The Ejection Fraction is the most important baseline measurement of the function of the left ventricle. One method of determining the Ejection Fraction is by cardiac catheterization. However, cardiac catheterization is an invasive technique, requires extensive dedicated space and equipment usually in a hospital setting, is time consuming, and has some inherent morbidity and mortality. Cardiac catheterization is also of no practical use during ambulatory examination due to the stationary nature of the data acquisition equipment.

Certain noninvasive methods, such as echo-cardiographic and radionuclide techniques, exist, but these procedures are inordinately expensive. Also, these procedures have limiting factors in ambulatory diagnosis or the collection of data outside of the dedicated cardiovascular environments.

Another noninvasive method of determining the Ejection Fraction, and hence left ventricular performance, is to collect a plurality of time-based measurements known as Systolic Time Intervals, or STI. The Ejection Fraction is a function of STI. The STI values are derived by first taking readings from arterial pulse tracing, phonocardiogram, and electrocardiogram (ECG) and then calculating STI. This method, while being relatively economical, is limited by the accuracy of the data received from currently used measuring devices, and moreover requires cumbersome post measurement computations that delay results. State-of-the-art techniques are not designed to allow readings in substantially real time, real time, or during ambulatory examination.

A definite need exists for a non-invasive, automated, real time method of, and apparatus for, making STI and EF measurements in an accurate, economical, and repeatable manner while the patient is either inactive or ambulatory. A need also exists for the collection of this data by a portable device outside of the hospital or physician's office.

SUMMARY OF THE INVENTION

The present invention provides an apparatus and method for accurately measuring and processing key physiological parameters necessary to yield real time left ventricular performance based on Left Ventricular Ejection Time (LVET), Electromechanical Systole (EMS), Systolic Time Interval (STI) and Ejection Fraction (EF). Specifically, LVET and EMS values are used to derive STI values which, in turn, yield EF values.

Electrical signals representing the certain key physiological functions are developed by a plurality of physiological signal sensing devices. These sensing devices produce signals representing arterial pulse values, phonocardiographic values, and electrocardiographic values. The arterial pulse values are preferably developed from sensing devices which measure patient volume oscillometric pulse waves and/or doppler pulse waves. All of the above signals are uniquely conditioned and, using the same or substantially the same time base, combined in a manner that yields "real time" outputs of EMS, LVET, STI and EF values.

Specifically, the electrocardiographic waveforms and phonocardiographic waveforms provide the EMS values. One of either the volume oscillometric pulse waveforms or the doppler pulse waveforms provide the LVET value. In an alternate embodiment, the LVET value is derived from an average arterial pulse wave which is a function of both the volume pulse oscillometric wave and the doppler pulse wave.

After the EMS and LVET values are processed, the STI values are derived based on the above EMS and LVET values. Then, the EF values are derived from the STI values.

In a preferred embodiment, prior to derivation of the STI and EF values, the EMS and LVET values are processed by conditioning constituent signals to assess a mean signal value averaged over a predetermined number of heartbeats, and to exclude any signal values which are outside a predetermined mathematical range, for example, two standard deviations from the mean signal value.

In a preferred embodiment, the EMS, LVET, STI and EF values can be viewed on a monitor side-by-side with analog waveforms representing the immediate physiological state of the patient. The EMS, LVET, STI, EF and related sensor outputs may also be stored in memory for subsequent processing.

The noninvasive aspect of the sensors allows ambulatory examination with no patient discomfort. The signals provided by the sensors are processed at a speed sufficient to provide "real time" evaluation of the ambulatory patient's condition. As the terms are used herein, "real time" and "substantially real time" mean that the constituent signals that contribute to the LVET, STI, and EF are all referenced to the same or substantially the same time base so that the results reflect the actual collective averaged physiological parameters of the patient, even though the constituent signals and/or processed EMS, LVET, STI and/or EF are delayed (i.e., 3–20 seconds depending on heart rate) or stored for later playback or processing. It is also understood that the term "sensor" used herein includes the physiological sensing device per se as well as the associated circuitry which uniquely conditions and combines the physiological signals.

The phonocardiographic sensor, in the preferred form, has circuitry capable of processing signals more accurately by reducing the amount of background noise impingement on the sensor transducer, such as provided by a microphone. Specifically, the noise reduction phonocardiographic sensor includes a sound pick-up housing having a first microphone means which receives both the heart sound and background noise, and a second microphone means which receives only background noise. The signals from the above microphone means are processed through separate filter means. An inverting amplifier means receives the signal which originates from the background-noise-only microphone, after which it is added to the heart sound plus background noise signal, thus canceling the background noise. The enhanced heart sound signal is then passed through a band pass filter means having a variable response, a gain control potentiometer means, a gain stage and into the signal acquisition board. The reduced noise signal from the phonocardiographic sensor provides a measurement of the aorta's second heart sounds. The EMS values are based on the second heart sound values along with the initiation points of the cardiac wave processed by the electrocardiographic sensor, discussed below.

Two sensors are preferably used to provide artery pulse tracing signals. These sensors include a multi-crystal piezoelectric doppler pulse wave sensor, and a volume oscillometric pulse wave sensor. More accurate pulse tracing can be ascertained with these two sensors because the signals of the sensors can be processed to derive an average arterial pulse wave. However, if the signals from one of the two sensors is outside a predetermined standard deviation value, this abnormal signal is disregarded. In combination these sensors provide signals representing the patient's arterial pulse wave initiation points and dicrotic notches. Alternatively, one of the two signals can be selected for processing to derive arterial pulse wave initiation points and dicrotic notches. The LVET values are based on the arterial pulse wave initiation points and dicrotic notches.

The multi-crystal piezoelectric doppler pulse wave sensor preferably has circuitry capable of processing signals more accurately than conventional arterial pulse wave sensors. Specifically, the sensor includes an oscillator means. The signal from this oscillator means passes into a send crystal means. The oscillator means also provides the carrier for a demodulator means. A receive crystal means sends a modulated signal to the demodulator means whereby a change in frequency of the amplified output signal represents the velocity of the patient's blood flow.

The volume oscillometric pulse wave sensor preferably has circuitry capable of accurately processing pressue pulse wave signals. Specifically, the sensor includes a pressure transducer means that is in line with the pressure hose on a conventional blood pressure cuff. The pressure transducer means is connected to an isolation amplifier means. A portion of the signal from the isolation amplifier means passes into a low pass filter means and then to the acquisition board where the systolic blood pressure and diastolic blood pressure signals are provided. The remainder of the signal from the isolation amplifier means passes through a capacitor means, a high pass filter means, a gain stage and a low pass filter means. The signal then passes through a baseline clamping diode means and another gain stage and is then received by the acquisition board where the dicrotic notch pulse wave is provided.

The sensor providing electrocardiographic signals receives signals based on the patient's onset of QRS-Q'R'S' peaks (the initiation points of the electrocardiogram waves). The EMS values are based on the onset of QRS-Q'R'S' values, along with the cardiac wave initiation points from the phonocardiographic sensor. Heart rate values are also based on the onset of QRS-Q'R'S' values.

All of the above conditioned signals are then converted to digital values by an analog-to-digital converter means and fed to a central processing means where EMS, LVET, STI and EF values are derived. But first, the central processing means processes digital values based on the onset of QRS-Q'R'S' signals from the electrocardiographic sensor to provide heart rate values. A mean heart rate value over a predetermined number of heart beats is ascertained based on these heart rate values. The mean heart rate value is required for EMS, LVET, STI and EF value derivation by the central processing unit means.

The central processing means then determines an Electromechanical Systole value (EMS) by processing digital values of signals representing the cardiac initiation QRSQ'R'S' Q'R'S' peaks of the electrocardiogram waves and digital values of the high frequency components of the second heart sound signals from the phonocardiographic sensor. Preferably, a mean EMS value is derived based on the EMS values over a predetermined number of heart beats, and a refined EMS value is ascertained based on EMS values within two standard deviations from the mean EMS value. The central processor means then corrects the refined EMS value, from lookup tables based on patient sex, as a function of the heart rate value above.

Either the volume oscillometric pulse wave sensor signals or the multi-crystal piezoelectric doppler pulse wave sensor signals may be selected for processing by the central processing means to derive Left Ventricular Ejection Time (LVET) values. In the alternative, the central processing unit can combine the digital values of the volume oscillometric pulse wave sensor signals and the multi-crystal piezoelectric doppler pulse wave sensor signals to yield an average arterial pulse wave value. The central processor means derives an LVET value based on the arterial pulse wave initiation point signals and the digital values of the arterial pulse wave dicrotic notch signals from either the previously derived average arterial pulse wave, or from one of the two volume oscillometric pulse wave or doppler pulse wave signals. Preferably, a mean LVET value is derived based on the LVET values over a predetermined number of heart eeats, and a refined LVET value is ascertained based on LVET values within two standard deviations from the mean LVET value. The central processor means then corrects the refined LVET value, based on patient sex, as a function of the heart rate value previously derived.

A Systolic Time Interval (STI) value is provided by the central processor means as a function of the mean heart rate value, the corrected Electromechanical Systole value and the corrected Left Ventricular Ejection Time value.

Finally, the central processor means derives the Ejection Fraction (EF) value based on the Systolic Time Interval value.

A signal display means generates visual wave forms based on the outputs of the above mentioned sensors, and displays EMS corrected, LVET corrected, EMS, LVET, LVET doppler, heart rate, EF and EF average values, all with respect to synchronous time base, or bases.

In a preferred embodiment, the signal conditioning circuitry of the above sensors is physically separate from the sensing devices. The sensing devices which collect physiological information can thus be attached to an ambulatory patient. Further, the physiological data can be collected from the patient outside of the clinical environment. In this embodiment, the signals from the sensing devices are processed by an encoding means prior to entering a record/playback means. This raw data may be processed at a later date in the hospital, office, or clinic where the above record/playback means is connected to a signal conditioning means having the above mentioned conditioning circuitry of the previously described sensors. The conditioned signals then enter the above mentioned analog-to-digital converter and are processed by the CPU for subsequent display on a monitor, as detailed previously.

In another embodiment of the present invention, a telemetry transmitting means is connected to the sensing devices on the patient. This telemetry transmitting means transmits signals to a remote telemetry receiving means connected to a signal conditioning means. The signals are then processed as detailed above. In this embodiment, the patient cardiac function can be monitored and assessed in real time even though the patient is physically remote from the signal conditioning means and the central processing means.

In still another preferred embodiment of the present invention, sensors collecting blood oxygenation and skin temperature also provide signals to the central processing means, and are displayed along with the cardiac parameters so as to indicate the overall physical state of the patient.

These and other features and advantages of the invention will become apparent in the detailed description and claims to follow, taken in conjunction with the accompanying drawings.

BRIEF DESCRIPTION OF DRAWINGS

FIG. 3b is another perspective view of the sound pick-up of the phonocardiographic sensor taken at line 3b—3b of FIG. 3a.

FIG. 8 is a perspective view of the positioning of the blood pressure cuff of the oscillometric pulse wave sensors, and of the head of the multi-crystal piezoelectric doppler pulse wave sensor on a patient.

FIG. 10 is an electronics schematic of the volume oscillometric pulse wave sensor.

FIG. 19, 19A, 19B is a flow chart of the ejection fraction analyzing computer program.

DETAILED DESCRIPTION OF THE INVENTION

General Operation

Figure 1:
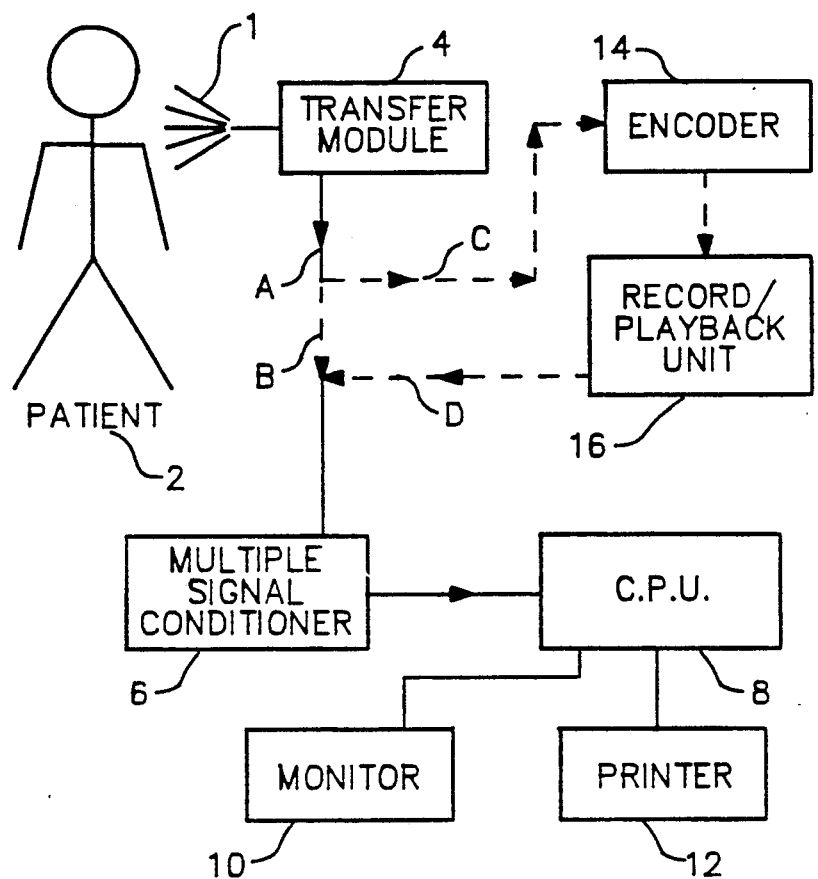
FIG. 1 is a block diagram of the apparatus for sensing cardiac performance.

Referring initially to FIG. 1, a block diagram shows one preferred embodiment of the apparatus for collecting and processing physiological data in real time. A plurality of physiological signal sensing devices 1 that are associated with phonocardiographic, multi-crystal piezoelectric doppler pulse wave, volume oscillometric pulse wave, and electrocardiographic sensing devices (described in detail below), are placed on patient 2. As described in detail below, the term "sensors" used herein includes the physiological sensing devices 1 as well as the associated circuitry which uniquely conditions and combines the physiological signals. These physiological signal sensing devices 1 are connected by plugs and wires to transfer module 4, which is also preferably on patient 2. Transfer module 4 may include conventional switches to select between various electrocardiogram sensors in order to obtain the strongest and hence most reliable physiological signal. Transfer module 4 also includes the volume oscillometric pressure transducer, air pump, and pressure release valve described in greater detail below.

Transfer module 4 is connected to a multiple channel analog-to-digital signal conditioner 6 which contains circuitry for conditioning the plurality of signals from the physiological signal sensing devices 1. Specifically, in the present embodiment, signals pass from transfer module 4 to multiple signal conditioner 6 along signal path A-B. However, as described in the following embodiment, switched or plug-in connectors may also provide alternate signal path C-D. A power source in multiple signal conditioner 6 activates a series of preamplifiers and powers the various sensors. The physiological signals pass through a stabilizing amplifier and a Data Acquisition System Direct Current (DAS-DC) input. The multiple signal conditioner 6 allows selection of the specific sensor signals which are to enter the stabilizing amplifier. Multiple signal conditioner 6 also includes an analog-to-digital converter (described below) which processes the signals into digital form.

The analog-to-digital converted signals from signal conditioner 6 are then processed by a central processing unit 8 in order to provide signals representing Electromechanical Systole, Left Ventricular Ejection Time, Systolic Time Interval and Ejection Fraction values which are displayed on a separate tape based or solid state monitor 10 or on printer 12, along with the analog levels of the sensors. These numerical and analog values are displayed in substantially real time and with the same time base. Central processing unit 8, above, may be provided by a conventional computer system.

FIG. 1 also shows an optional embodiment of the apparatus for collecting and processing physiological data which allows data collection outside of the clinical environment as well as data collection of ambulatory patients. As in the previously described embodiment, the signals from physiological signal sensing devices 1 are fed to transfer module 4. However, in this optional embodiment, the signals from transfer module 4 take path C-D instead of path A-B. Then, on-patient encoder 14 and record/playback 16 respectively code and retain the raw signals for processing at a later time in the practitioner's clinic, hospital or office. For processing, record/playback 16 is connected to previously described multiple signal conditioner 6. Signal conditioning, processing and analysis then occur in multiple signal conditioner 6, CPU 8, monitor 10 and/or printer 12 as previously described above.

Figure 21:
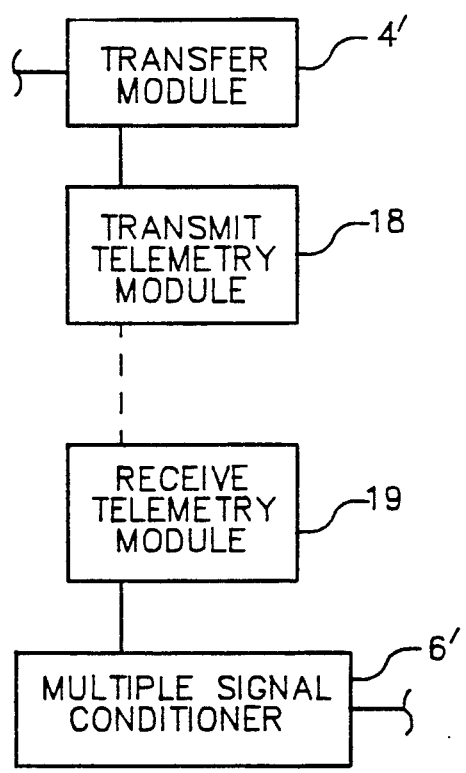
FIG. 21 is a block diagram of an alternate embodiment of the present invention showing telemetry components.

In yet another alternate embodiment shown in FIG. 21, the present invention can employ telemetry such that signals from transfer module 4' can be transmitted from a distance of a few feet to a number of miles. For example, these signals can thus be transmitted between distant locations within a hospital complex, such as from a patient location to a separate signal processing facility.

Referring to FIG. 21, sensor signals are received by transfer module 4' in the previously described manner. These signals are fed to transmit telemetry module 18 by transfer module 4'. Transmit telemetry module 18 sends these signals by radiowave over a distance to remotely situated receive telemetry module 19. The signals then are sent from receive telemetry module 19 to multiple signal conditioner 6' and are then processed as previously described. Transmit telemetry module 18 and receive telemetry module 19 are conventional, well known in the art and do not require further description.

Figure 2:
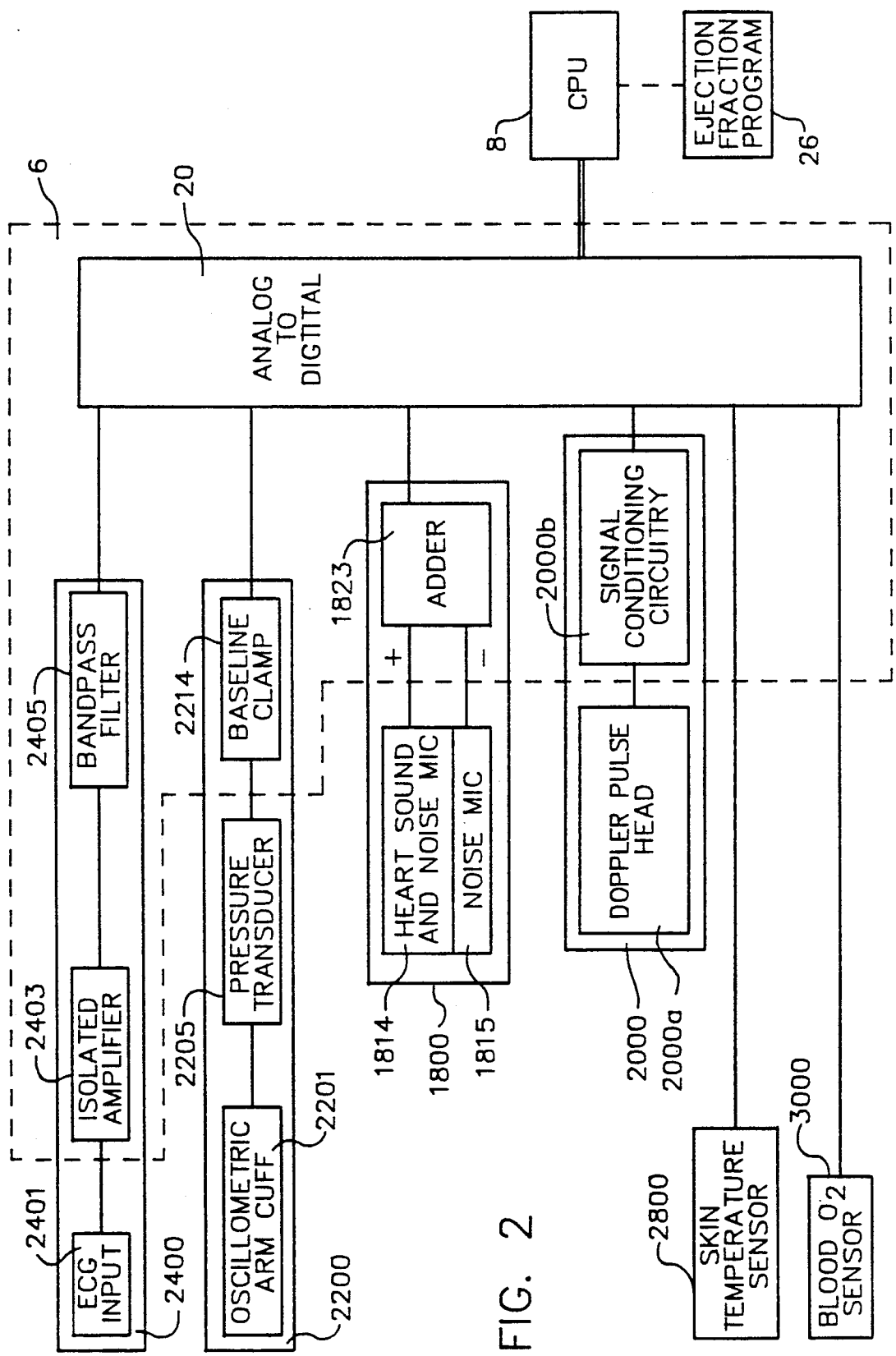
FIG. 2 is a block diagram of the sensors, analog-to-digital multiple signal conditioner and central processing unit of the apparatus of the subject invention.

FIG. 2 is a block diagram showing the components of the apparatus of the present invention which specifically pertain to signal collection and signal processing. The sensors of FIG. 2, the elements of which process a particular signal, may actually be in physically separate locations. These sensors include the physiological signal sensing devices as well as the associated conditioning circuitry. However, these sensor elements are shown adjacent to each other in FIG. 2 to describe the signal processing pathways of the present invention. For example, referring to electrocardiographic sensor 2400 of FIG. 2, the ECG input 2401 is a physiological sensing device placed on patient 2 of FIG. 1, while isolated amplifier 2403 and band pass filter 2405 of FIG. 2 are part of the signal conditioning circuitry of multiple signal conditioner 6 of FIG. 1.

Also, referring to volume oscillometric pulse wave sensor 2200, oscillometric cuff 2201 is placed on the arm of patient 2 of FIG. 1, pressure transducer 2205 is a physiological signal sensing device located in transfer module 4 of FIG. 1, and baseline clamp 2214 is a portion of the signal conditioning circuitry of multiple signal conditioner 6 of FIG. 1.

Likewise, phonocardiographic sensor 1800 includes microphones 1814 and 1815, which are physiological signal sensing devices placed on patient 2 of FIG. 1, and adder 1823 which is a portion of the signal conditioning circuitry of multiple signal conditioner 6 of FIG. 1.

Doppler pulse wave sensor (preferably multi-crystal piezoelectric type) 2000 has physiological signal sensing crystals located in a head 2000a remote from the signal conditioning circuitry, as explained in detail below. The signal conditioning circuitry 2000b is located within multiple signal conditioner 6 and is discussed in greater detail below.

As shown in FIG. 2, the signals from electrocardiographic sensor 2400, volume oscillometric pulse wave sensor 2200, phonocardiographic sensor 1800, and doppler pulse wave sensor 2000 are converted into digital signals by analog-to-digital converter 18. Analog-to-digital converter 18 is preferably located in multiple signal conditioner 6 of FIG. 1.

After being digitized by analog-to-digital converter 20, all of the above signals are processed in the central processing unit 8 based on Ejection Fraction program 26.

In a preferred embodiment, skin temperature sensor 2800 and blood oxygen sensor 3000 (preferably including an ear oximeter having a light source and a light sensor) also provide signals to analog-to-digital converter 20.

Phonocardiographic Sensor

Figure 3A:
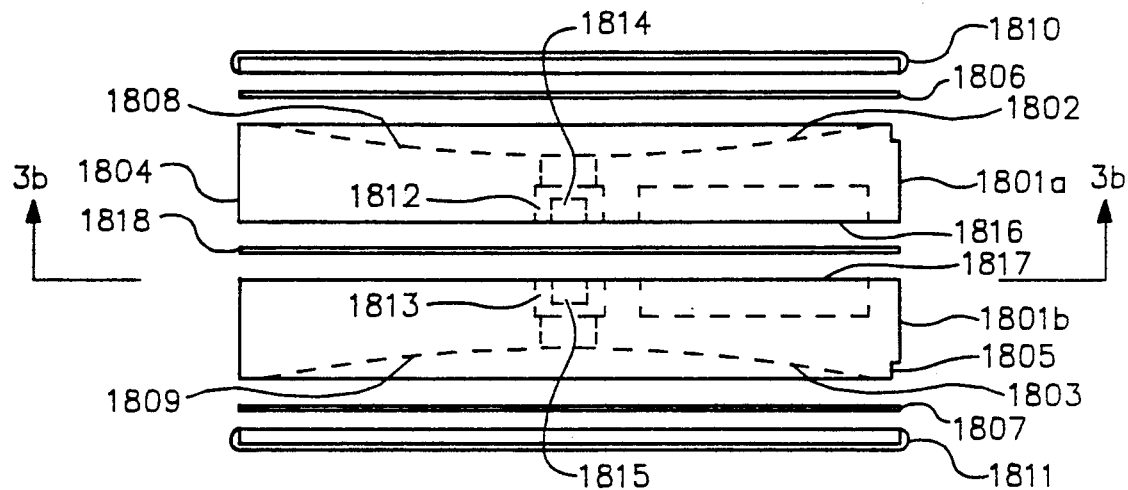
FIG. 3a is a perspective view of the sound pick-up of the phonocardiographic sensor.
Figure 3B:
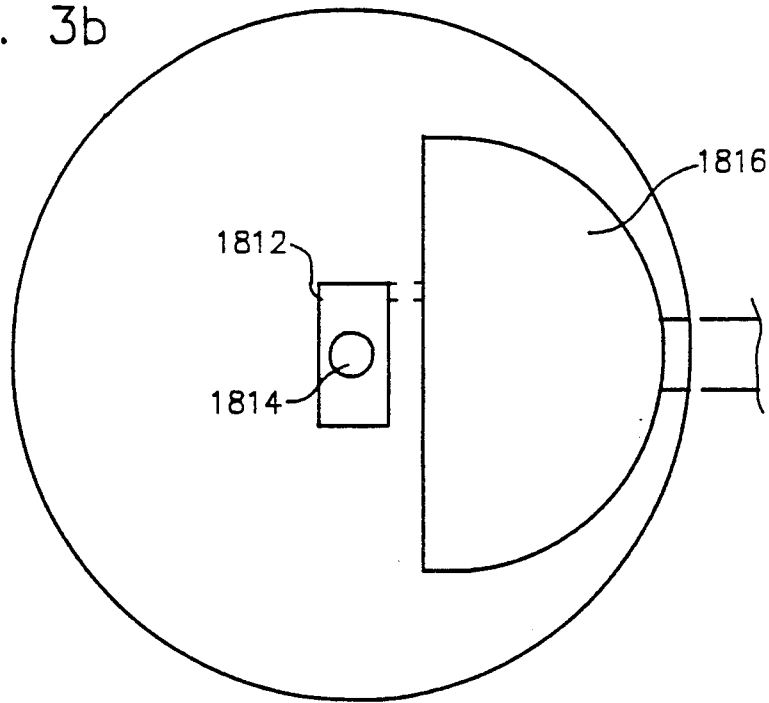
Figure 4A:
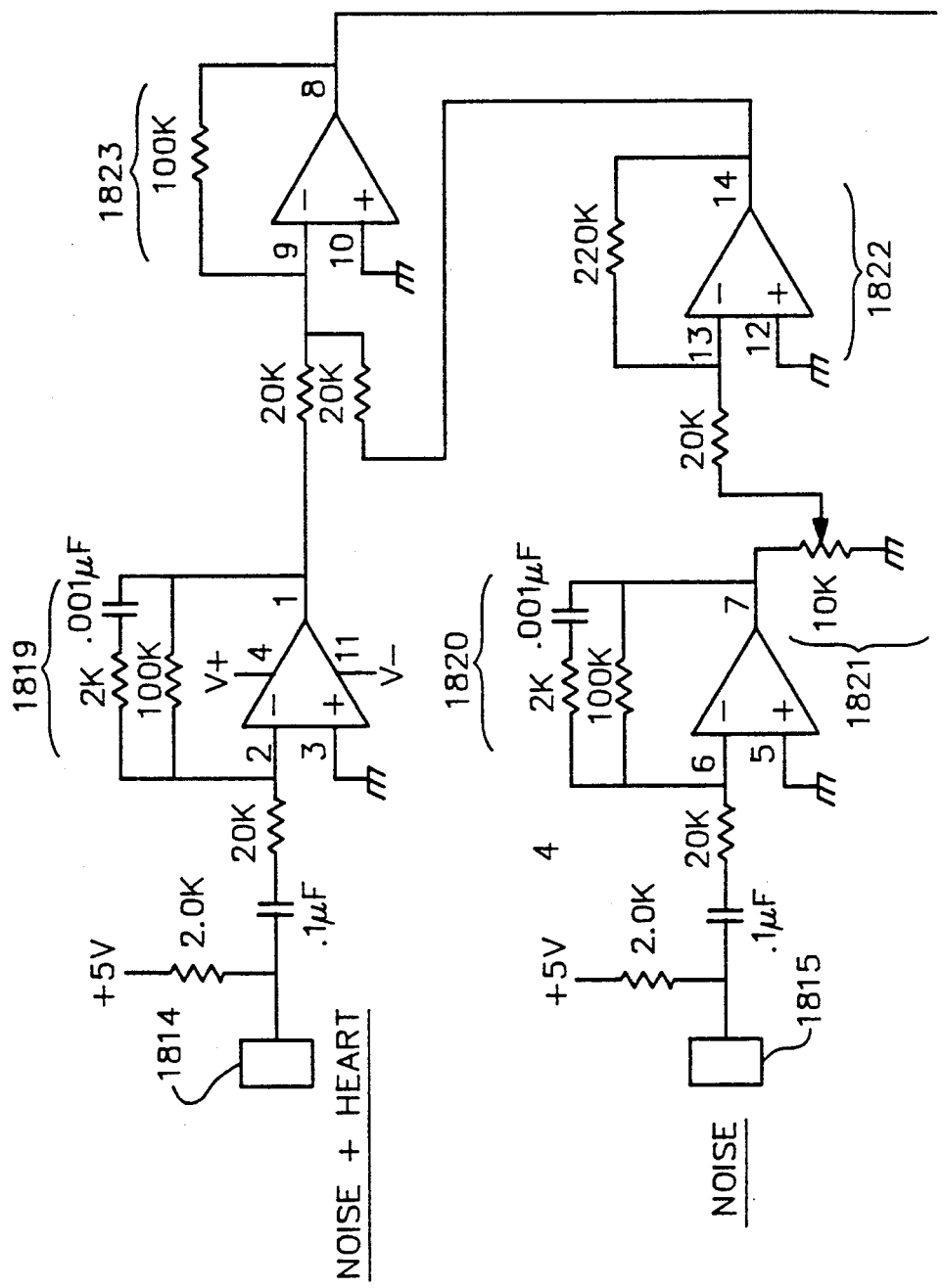
Figure 4B:
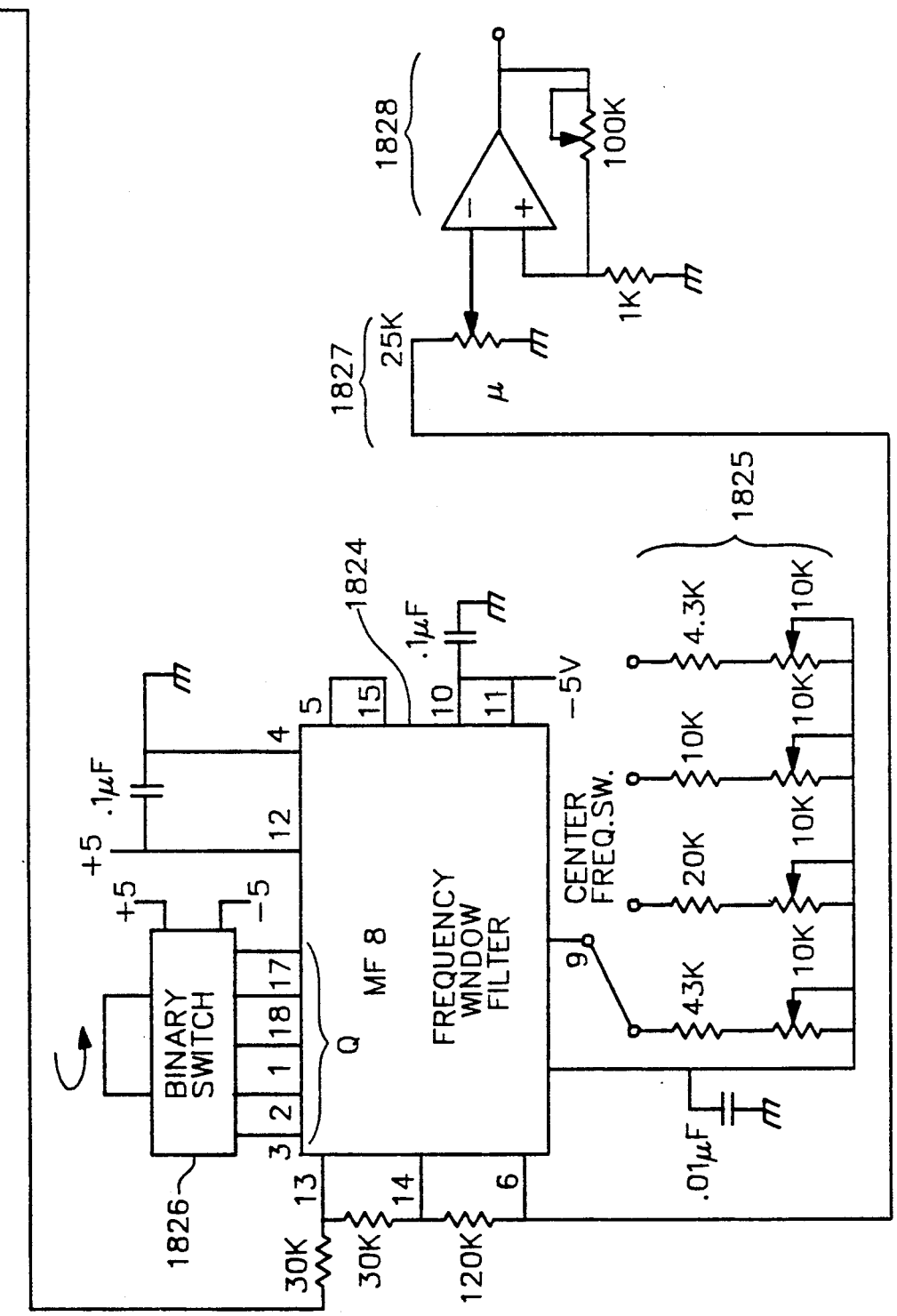

FIGS. 3a and 3b show the sound pick-up of the phonocardiographic sensor 1800, including body portions 1801a and 1801b which have concave faces 1802 and 1803, respectively. Body portions 1801a and 1801b also have threads 1804 and 1805, respectively. Diaphragms 1806 and 1807 fit over concave faces 1802 and 1803, respectively, to form sound chambers 1808 and 1809. Rings 1810 and 1811 secure diaphragms 1806 and 1807 to body portions 1801a and 1801b through threaded connection with threads 1804 and 1805. Microphone chambers 1812 and 1813, located under concave faces 1802 and 1803, respectively, contain microphones 1814 and 1815. Wiring from microphones 1814 and 1815 is housed in wire chambers 1816 and 1817. Body portions 1800 and 1801 are connected by center shield 1818 to form a single phonocardiographic sensor 1800. Center shield 1818 is comprised of a material having sufficient sound absorbing properties such that chambers 1808 and 1809 are substantially sound-proof with respect to each other. Examples of materials employed substantially for center shield 1818 are Valox TM by General Electric and/or similar materials such as U.H.M.W. (Ultra-High Molecular Weight Polymer).

Figure 4:
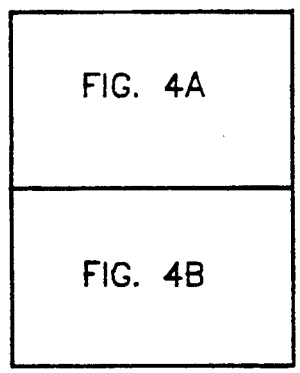
FIG. 4, 4A, 4B is an electronics schematic of the phonocardiographic sensor.

Referring to FIG. 4, the electronics schematic of the phonocardiographic sensor 1800 signal conditioning circuitry, microphone 1814 receives both noise and the heart sound. This signal passes into a band pass filter 1819 which has a response from 10 hertz to 1000 hertz. The band pass filter 1819 is also a buffer amplifier. The second microphone 1815 is a noise only microphone. Microphone 1815 leads to another buffer amplifier 1820 having identical filter response (from 10 hertz to 1000 hertz) as band pass filter 1819. Next, a 10 kohm potentiometer 1821 connected to buffer amplifier 1820 leads to an inverting amplifier 1822. Connected to both the noise and noise plus heart sound circuits is a summing circuit (adder) 1823 where the inverted noise is added to the signal combining the noise and the heart sound. Thus the noise is cancelled and just the heart sound remains. The heart sound signal then passes through a narrow band pass filter 1824. The filter response can be altered, by the frequency switch 1825, between the frequencies of 25, 50, 100 and 200 hertz. The binary switch 1826 on the band pass filter 1824 selects the Q value which, in turn, sets the window size of the band pass filter 1824. The heart sound signal then passes through the gain control potentiometer 1827 and a final gain stage 1828 before it passes into the acquisition board.

Multi-crystal Piezoelectric Doppler Pulse Wave Sensor

Figure 5A:
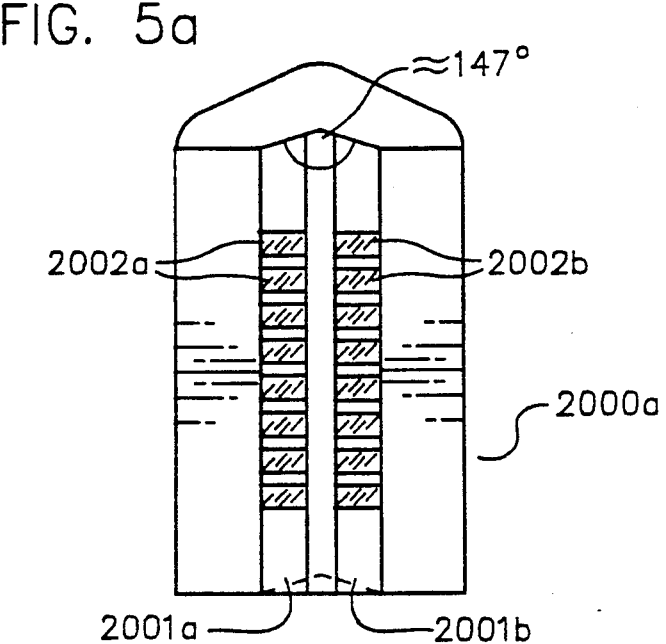
FIG. 5a is a perspective view of the head of the multi-crystal piezoelectric doppler pulse wave sensor.
Figure 5B:
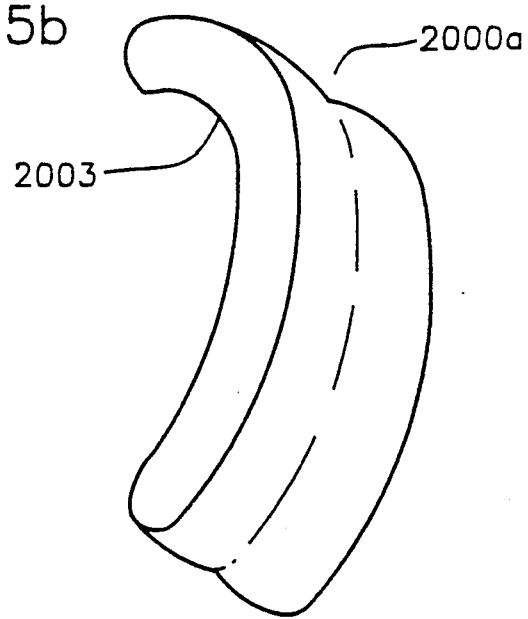
FIG. 5b is another perspective view of the head of the multi-crystal piezoelectric doppler pulse wave sensor.

FIGS. 5a and 5b show the head 2000a of the multi-crystal piezoelectric doppler pulse wave sensor 2000, including channels 2001a and 2001b which contain a plurality of piezoelectric crystals 2002, preferably in two parallel rows, one transmit crystal row 2002a and one receive crystal row 2002b. Preferably channel 2001a and 2001b each hold eight piezoelectric crystals in crystal rows 2002a and 2002b. However, the crystal number and orientation can vary based on, for example, the size and shape of the crystals employed. Channels 2001a and 2001b are angled such that the crystal faces of transmit crystal row 2002a and receive crystal row 2002b form an obtuse angle, preferably of approximately 147°. Thus, sound waves of between 5 and 8 magaHz are sent by transmit crystal row 2002a a distance of approximately one inch through the patients arm to a focal point in the patient's artery where the sound signal is reflected off of blood cells. This angle of reflection is approximately 33°. The frequency of the reflected wave is a function of blood cell velocity, which in turn is a measure of artery blood pressure. The typical frequency shift of an 8.000 megaHz wave is to a frequency of between 8.001 and 8.020 megaHz. The frequency shifted sound wave is then received by at least one crystal in receive crystal row 2002b.

As shown in FIG. 5b, the head of sensor 2000 has contoured face 2003 adapted to fit the contours of a portion of the patient's body, such as the upper arm. As shown in FIG. 8, the head of sensor 2000 is placed on the patient's arm so that crystal rows 2002a and 2002b are perpendicular with artery A. This orientation maximizes sensor efficiency because it ensures that at least one transmit crystal and one receive crystal will be in alignment with artery A. Note that the alignment of only one transmit and one receive crystal over artery A will often allow the accurate collection of physiological signals.

However, when movement of artery A occurs relative to a plurality of pairs of send and receive crystals, a first pair of send and receive crystals may process only a portion of a single physiological signal with the remainder of the single physiological signal being processed by one or more other send and receive crystal pairs. Thus a plurality of timed segments of various send and receive crystals may produce a doppler pulse wave for a single heart beat.

The crystals used in piezoelectric crystal rows 2002a and 2002b are of a type known in the art such as PZT-5A, which is a lead zirconate titanate manufactured by Morgan Matroc, a division of Vernitron.

In an alternate embodiment, the piezoelectric crystal physiological signal sensing device can be a commercial unit having a single transmit crystal and a single receive crystal or a single crystal which is pulsed for alternately transmitting and receiving signals (e.g., the IMEXLAB 3000 by IMEX Medical Systems, Inc., or the Versatone Doppler Model D8 with P84 probe by Medasonics). These units, however, would be applicable to a non-ambulatory system.

Figure 6:
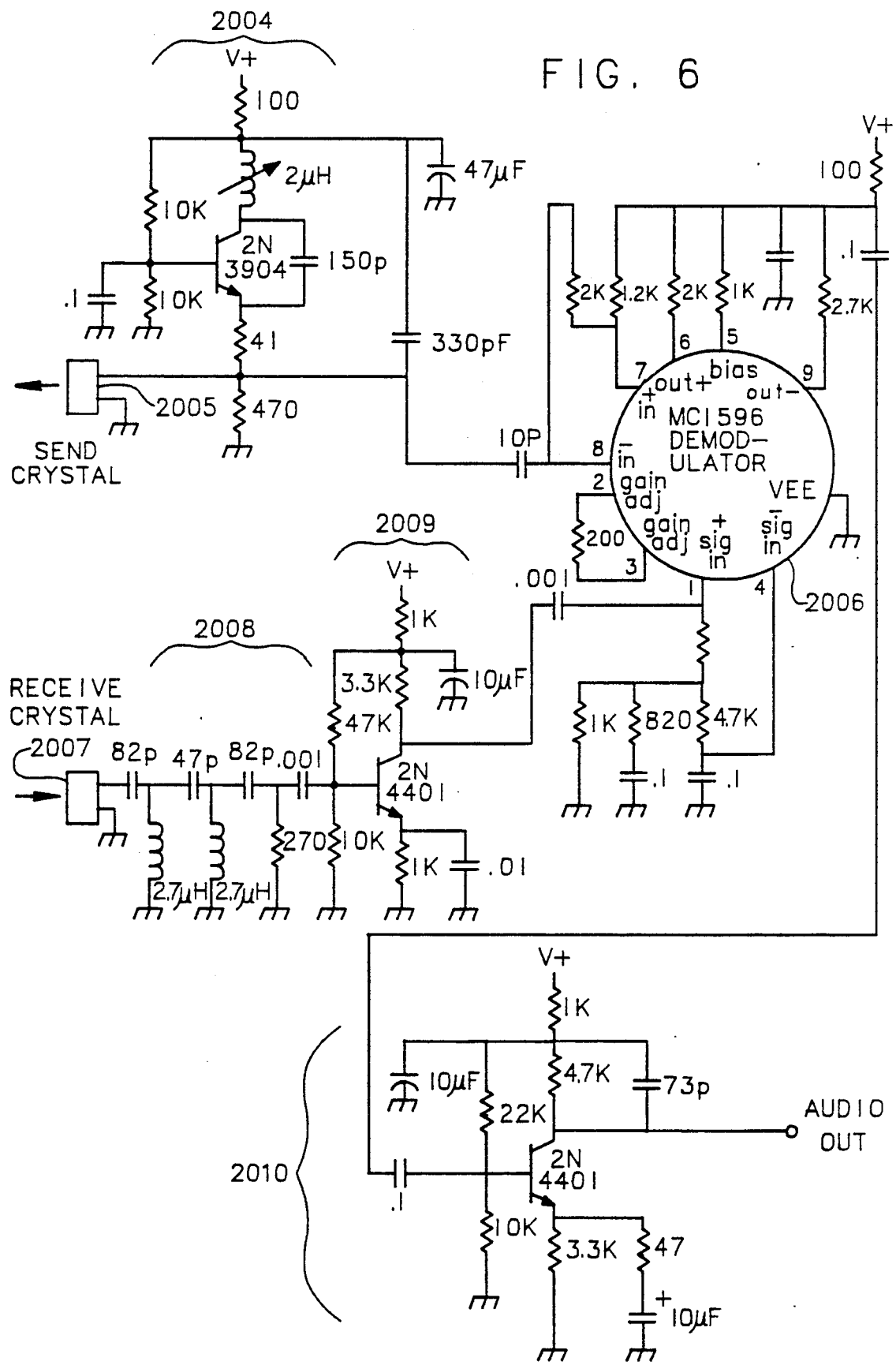
FIG. 6 is an electronics schematic of a pair of crystals from the multi-crystal piezoelectric doppler pulse wave sensor.

FIG. 6, shows the signal conditioning circuitry 2000b of the multi-crystal piezoelectric doppler pulse wave sensor 2000. The piezoelectric crystal send signal is developed by a Hartly oscillator 2004 which oscillates at 8 megahertz. The oscillator signal is coupled to the send crystal 2005. The Hartley oscillator 2004 also provides the carrier for the demodulator 2006. The receive crystal 2007 leads to an 8 megahertz band pass filter 2008. The signal from filter 2008 is then amplified by amplifier 2009 and sent to the demodulator 2006 as the modulating signal. The output of the demodulator passes into output amplifier 2010 which produces the difference signal, the frequency of which indicates the velocity of the blood flow. The dicrotic notch can be reliably detected from this wave.

Figure 7:
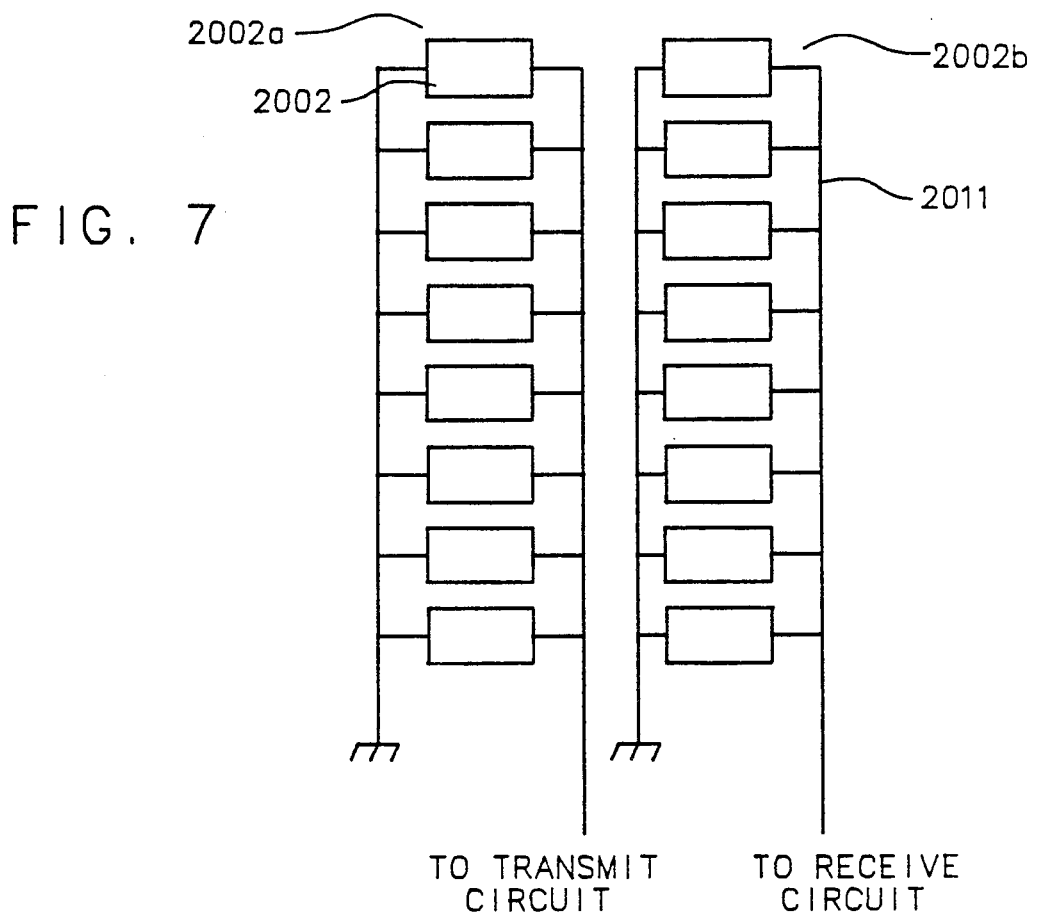
FIG. 7 is an electronics schematic of the wiring connecting the multi-crystal piezoelectric doppler pulse wave sensor crystals.

FIG. 7 shows the preferred wiring schematic of the multi-crystal piezoelectric doppler pulse wave sensor 2000, including piezoelectric crystal rows 2002a and 2002b and associated connections 2011. The transmit crystals are connected in parallel and driven by the transmit signal oscillator 2004, while the receive crystals are similarly wired in parallel for outputting the frequency shifts to filter 2008.

Volume Oscillometric Pulse Wave Sensor

FIG. 8 shows the preferred placement of the blood pressure cuff 2201 of volumetric oscillometric pulse wave sensor 2200, and of multi-crystal piezoelectric doppler pulse wave sensor 2000 over the proximal left axillary artery A.

Figure 9:
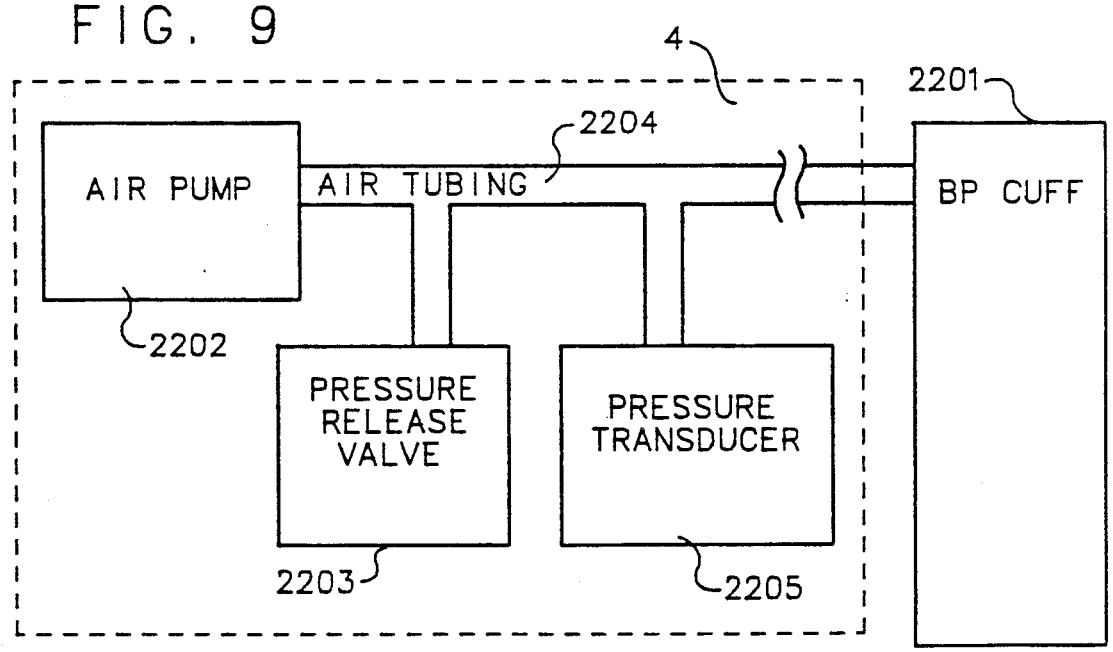
FIG. 9 is a block diagram of the volume oscillometric pulse wave sensor in a blood pressure sensor system.

FIG. 9 is a block diagram of the volume oscillometric pulse wave sensor 2200 in a blood pressure sensor system. Within transfer module 4, pressure transducer 2205 is situated downstream from air pump 2202 and pressure release valve 2203 in line with pressure hose 2204.

Referring to FIG. 10, an electronics schematic is shown of the signal conditioning circuitry for pulse wave sensor 2200. Pressure transducer 2205 is connected via a cable to an isolation amplifier 2206. Another cable 2207 couples the output of the isolation amplifier 2206 to a 10 hertz low pass filter 2208 which yields an output signal representing the pressure for the systolic and diastolic. The pressure valve signal passes to the acquisition board and bargraph so indicated.

An alternate signal branch passes through a 0.5 hertz high pass filter 2210, including a one microfared capacitor 2209, and then into a gain stage 2211 having a gain of 20. A potentiometer gain control couples the signal to a 30 hertz low pass filter 2212 having MF4 switch capacitor filters (fourth order filters). After low pass filter 2212, the signal is clamped at a baseline by clamp 2214 which is a diode that holds the signal voltage above zero. Finally, there is another gain stage 2215 which leads to the acquisition board, thus producing a signal representing the pulse wave that gives the dicrotic notch.

Electrocardiographic Sensor

Figure 11:
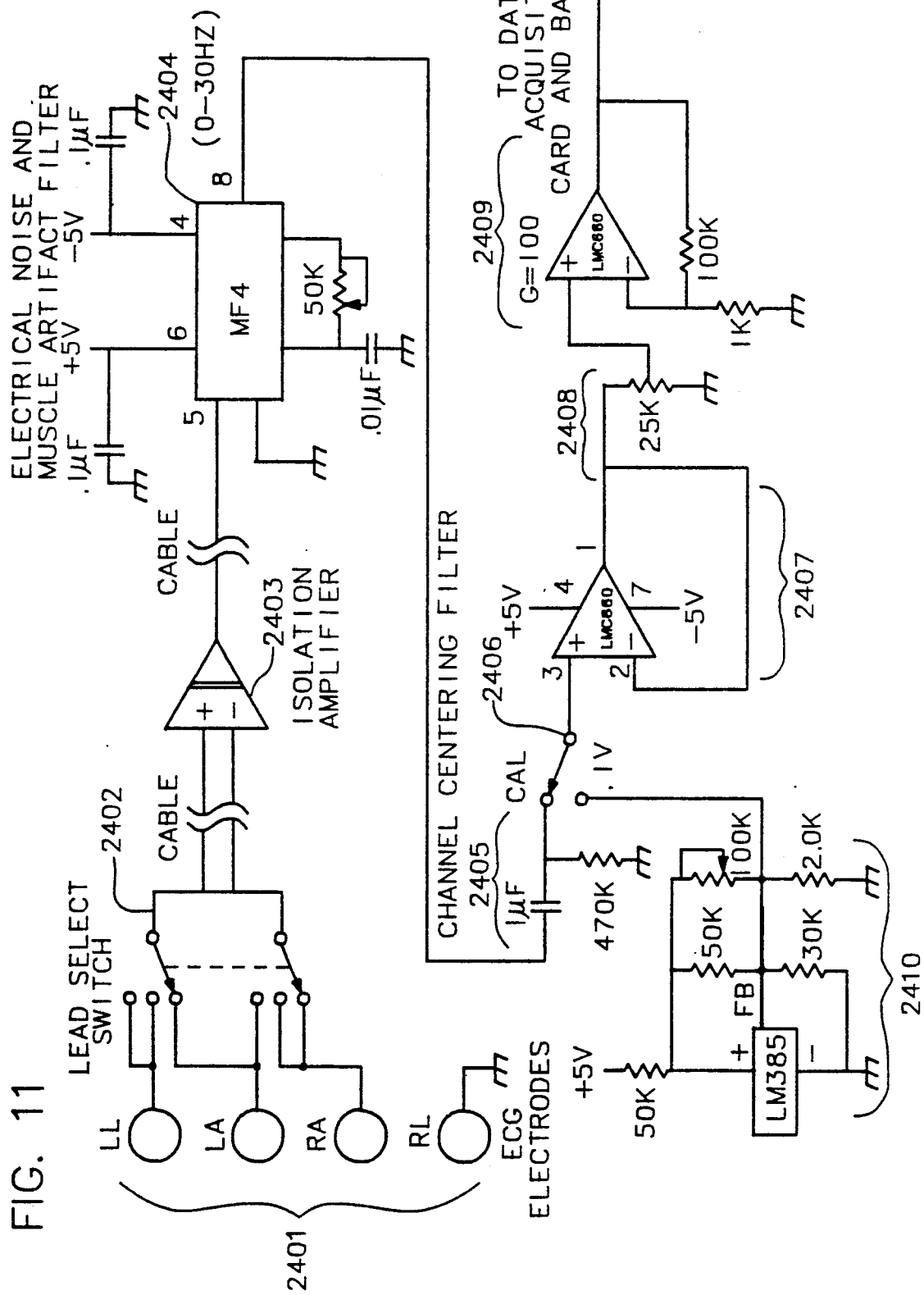
FIG. 11 is an electronics schematic of the ECG sensor.

The electrocardiographic sensor 2400 employs the signal conditioning circuitry shown in FIG. 11. Specifically, the electrodes 2401 are connected to the lead select switch 2402. Isolation amplifier 2403 protects the patient from electrical shock. An MF4 circuit 2404, which is a switch capacitor filter providing a low pass response of 30 hertz, is connected to the isolation amplifier 2403. A capacitor and a resistor form the channel centering filter 2405, which is a high pass filter having a corner frequency of about 0.5 hertz. After channel centering filter 2405, a switch 2406 selectively connects the signal path to a calibrator 2410, being a precision voltage reference set at 0.1 volts. When the switch 2406 is activated, 0.1 volts is applied by the calibrator 2410 to the signal path, thus forming a reference for the patient ECG. After switch 2406, the signal passes into a buffer amplifier 2407 and then into a gain control potentiometer 2408. Then the signal passes into a final gain stage 2409 and then into the acquisition board. Circuit 2410 is a precision voltage reference which gives the 0.1 volts.

Skin Temperature Sensor

Figure 12:
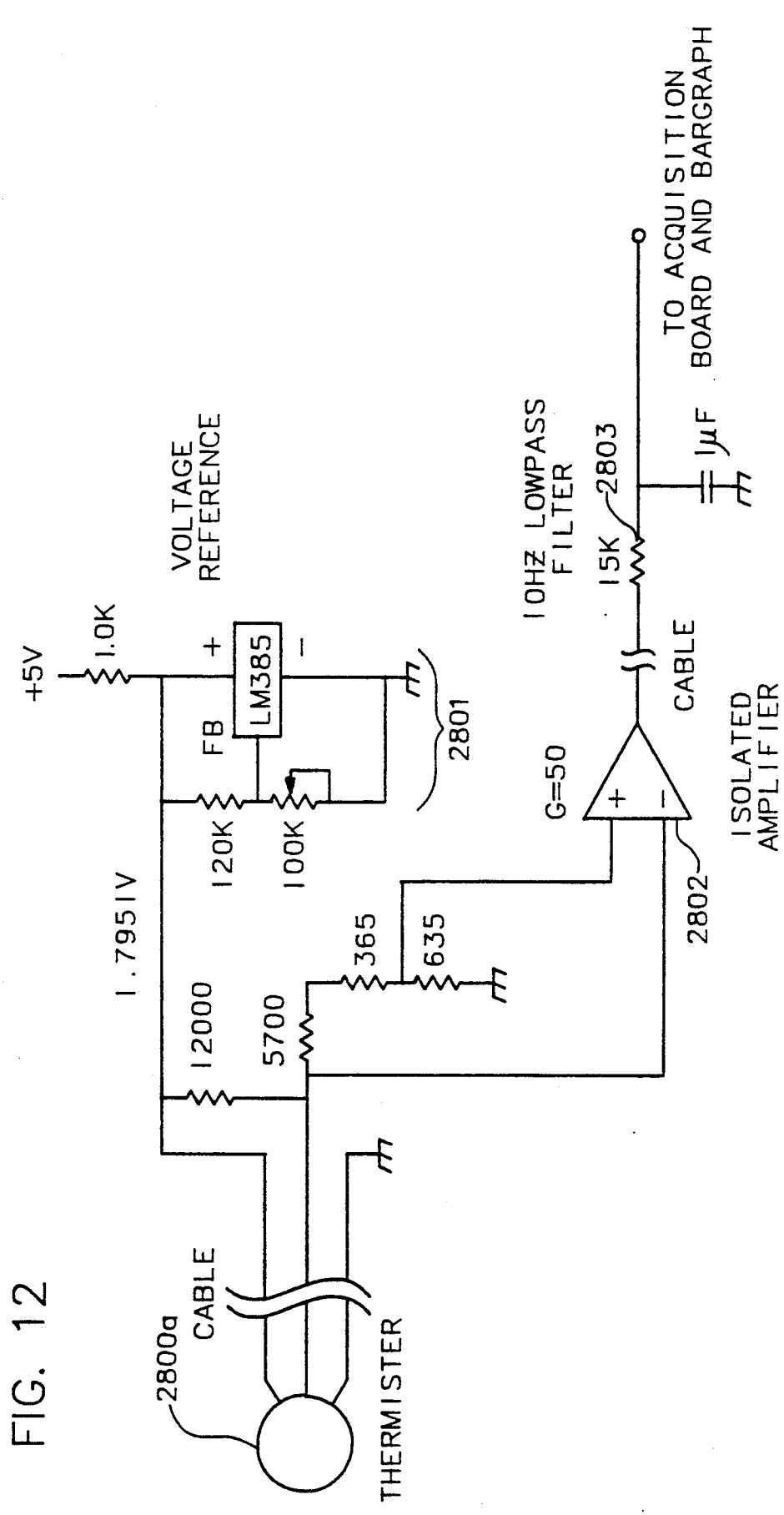
FIG. 12 is an electronics schematic of the temperature sensor.

Skin temperature sensor 2800 preferably includes the electronic circuitry of FIG. 12. Specifically, thermistor 2800a is attached to a resistor network 2801 which provides voltage between 0 and 100 millivolts, corresponding to the temperature range from 30° C. to 40° C., the range of human body temperature. The 100 millivolts signal at amplifier 2802 is amplified by 50 to obtain a 5 volt signal. A 10 hertz low pass filter 2803 cancels any noise.

Central Processing Unit Operation

A. Overview

Central processing unit 6 processes the signals received from the above described plurality of sensors and derives Left Ventricular Ejection Time (LVET), Electromechanical Systole (EMS), Systolic Time Interval (STI), and Ejection Fraction (EF) values based upon software program 30 as detailed in flow chart FIGS. 13-19.

The central processor 6 derives the EMS values based on the electrocardiographic sensor 2400 signals and the phonocardiographic sensor 1800 signals. To obtain the LVET values, the central processing unit 6 can process the volume oscillometric pulse wave sensor 2200 signals and multi-crystal piezoelectric doppler pulse wave sensor 2000 signals by either selecting one or the other signal, or by averaging both signals.

The central processing unit 6 processes LVET and EMS values by deriving mean values. The mean values are based on the collection of LVET and EMS values over a predetermined number of heart beats. The central processing unit 6 then excludes any values which are a predetermined mathematical range, for example, two standard deviations from the mean value.

Figure 20:
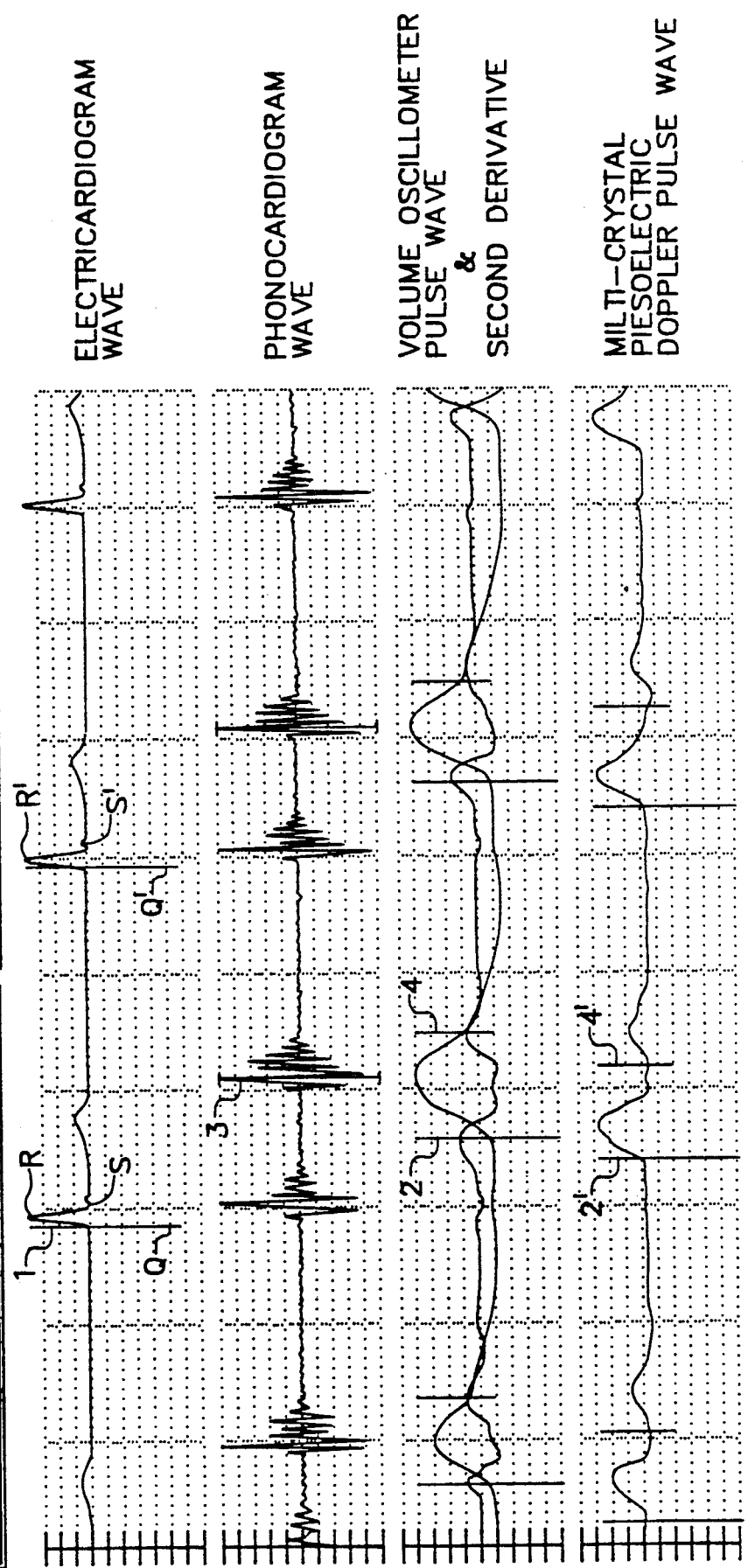
FIG. 20 is a graph of the output of the sensors of the subject invention.

Referring to FIG. 20, the central processing unit 6 derives key physiological data points from the electrocardiogram wave data, phonocardiogram wave data, volume oscillometric pulse wave data and dopper pulse wave data, and marks these key data points with flags.

FIG. 20 shows the electrocardiogram wave as the first wave form and shows flag 1 as the data point derived by the central processing unit 6 for the cardiac wave initiation point, i.e., QRS. The wave form ideally chosen is an electrocardiogram waveform with a first negative peak Q, a first positive peak R, and a second negative peak S, as shown in FIG. 20. FIG. 20 also shows a second electrocardiogram waveform after the first waveform. Central processor 6 derives the cardiac initiation point Q'R'S' of the second waveform. Central processor 6 then derives EMS values based on cardiac initiation points QRS and Q'R'S', and on the second heart sounds of the phonocardiogram wave, discussed next.

The second wave form of FIG. 20 is the phonocardiogram wave, and flag 3 is the data point derived by the central processing unit 6 for the high frequency component of the second heart sound.

The third wave form of FIG. 20 includes the volume oscillometric pulse wave and the waveform of its second derivative. Flag 2 of this third wave form shows the determination by central processing unit 6 of the arterial pulse wave initiation point based on the volume oscillometric pulse wave. Flag 4 of this third waveform shows the dicrotic notch data point based on the volume oscillometric pulse wave, as determined by central processing unit 6. The central processing unit 6 derives LVET values based on these arterial pulse wave initiation points and dicrotic notch points.

The fourth waveform of FIG. 20 shows the multi-crystal piezoelectric doppler pulse wave. Flag 2' shows the arterial pulse wave initiation point based on the doppler pulse wave as derived by the central processing unit 6. Flag 4' is the dicrotic notch data point of the doppler pulse wave, also derived by central processing unit 6.

Before ascertaining the above key data points having the above flags, the central processing unit 6 derives a heart rate value from the distance between the onset of a first QRS electrocardiogram waveform and the onset of a second Q'R'S' waveform. Central processing unit 6 then derives a mean heart rate value based on a plurality of heart rate values over a predetermined number of heart beats. This mean heart rate value is required to derive LVET and EMS values. It should be noted that the central processing unit 6 can also derive heart rate values based on the distance between the R and R' peaks or the S and S' peaks of two waveforms. Central processing unit 6 then derives the EMS, LVET, STI and EF values below based on the key data points and the mean heart rate value.

Specifically, the central processing unit 6 determines an Electromechanical Systole value (EMS) by processing digital values of signals representing the initiation points of the electrocardiogram cardiac waves and digital values of the high frequency components of the second heart sound signals from the phonocardiographic sensor (flag 3 minus flag 1 of FIG. 20). The central processing unit 6 derives a mean EMS value based on the EMS values over a predetermined number of heart beats, and a refined EMS value based on the EMS values which are within two standard deviations from the mean EMS value. In the first processing round, the standard deviation value is a predetermined value. In subsequent processing rounds, derived standard deviation values based on mean EMS values from previous processing rounds are employed. Preferably, the standard deviation of any processing round will be based on the mean EMS values of the two immediately prior rounds. The central processor unit 6 then corrects this refined EMS value, from look-up tables based on patient sex, as a function of the mean heart rate value, above, based on the formulas:

$EMS_{corrected} = EMS + 2.0$ HR where the patient is female;

$EMS_{corrected} = EMS + 2.1$ HR where the patient is male;

where
EMS = Electromechanical Systole value, and
HR = mean Heart Rate value

A Left Ventricular Ejection Time (LVET) value is provided by the central processor unit 6 as a function of the digital values of the arterial pulse wave initiation point signals and the digital values of the arterial pulse wave dicrotic notch signals from either the volume oscillometric pulse wave or the multi-crystal piezoelectric doppler pulse wave (flag 4 minus flag 2 or flag 4' minus flag 2' of FIG. 20). In an alternate embodiment, the values of both the volume oscillometric pulse wave and the multi-crystal piezoelectric doppler pulse wave are averaged to provide a derived average pulse wave.

The central processing unit 6 then ascertains a mean LVET value based on the LVET values over a predetermined number of heart beats and disregards any LVET values outside of, for example, two standard deviations of the mean LVET to provide a refined LVET value. In the first processing round, the standard deviation value is a predetermined value. In subsequent processing rounds, derived standard deviation values based on mean LVET values from previous processing rounds are employed. Preferably, the standard deviation value of any processing round will be based on the mean LVET values of the two immediately prior rounds.

The central processor means then corrects this LVET value, based on patient sex, as a function of the mean heart rate value previously derived:

$LVET_{corrected} = LVET + 1.6\ HR$ where the patient is female;

$LVET_{corrected} = LVET + 1.7\ HR$ where the patient is male;

where
LVET = Left Ventricular Ejection Time value, and
HR = mean Heart Rate value.

A Systolic Time Interval (STI) value is provided by the central processor unit 6 as a function of the mean heart rate value, the corrected Electromechanical Systole value and the corrected Left Ventricular Ejection Time value based on the formula:

$$STI = \frac{EMS_{corrected} - LVET_{corrected} + 0.4\ HR}{LVET_{corrected}}$$

where
$EMS_{corrected}$ = Electromechanical Systole Value$_{corrected}$;
$LVET_{corrected}$ = Left Ventricular Ejection Time$_{corrected}$; and
$Hr$ = mean Heart Rate value.

If the patient has Left Bundle Branch Block, or LBBB, the following formula for STI is used:

$$STI_{LBBB} = \frac{EMS_{corrected} - LVET_{corrected} + 0.4\ HR + 40}{LVET_{corrected}}$$

Finally, the central processor unit 6 derives the Ejection Fraction (EF) value based on the Systolic Time Interval value as follows:

$EF = 1.125 - STI1.25$ where STI = Systolic Time Interval value.

In an alternate embodiment, the volume oscillometric pulse wave values and the multi-crystal piezoelectric doppler pulse wave values are partitioned during processing such that separate doppler and non-doppler LVET, STI and EF values are obtained. These doppler and non-doppler values may then be averaged by central processing unit 6.

B. Primary Loop Program

Figure 13:
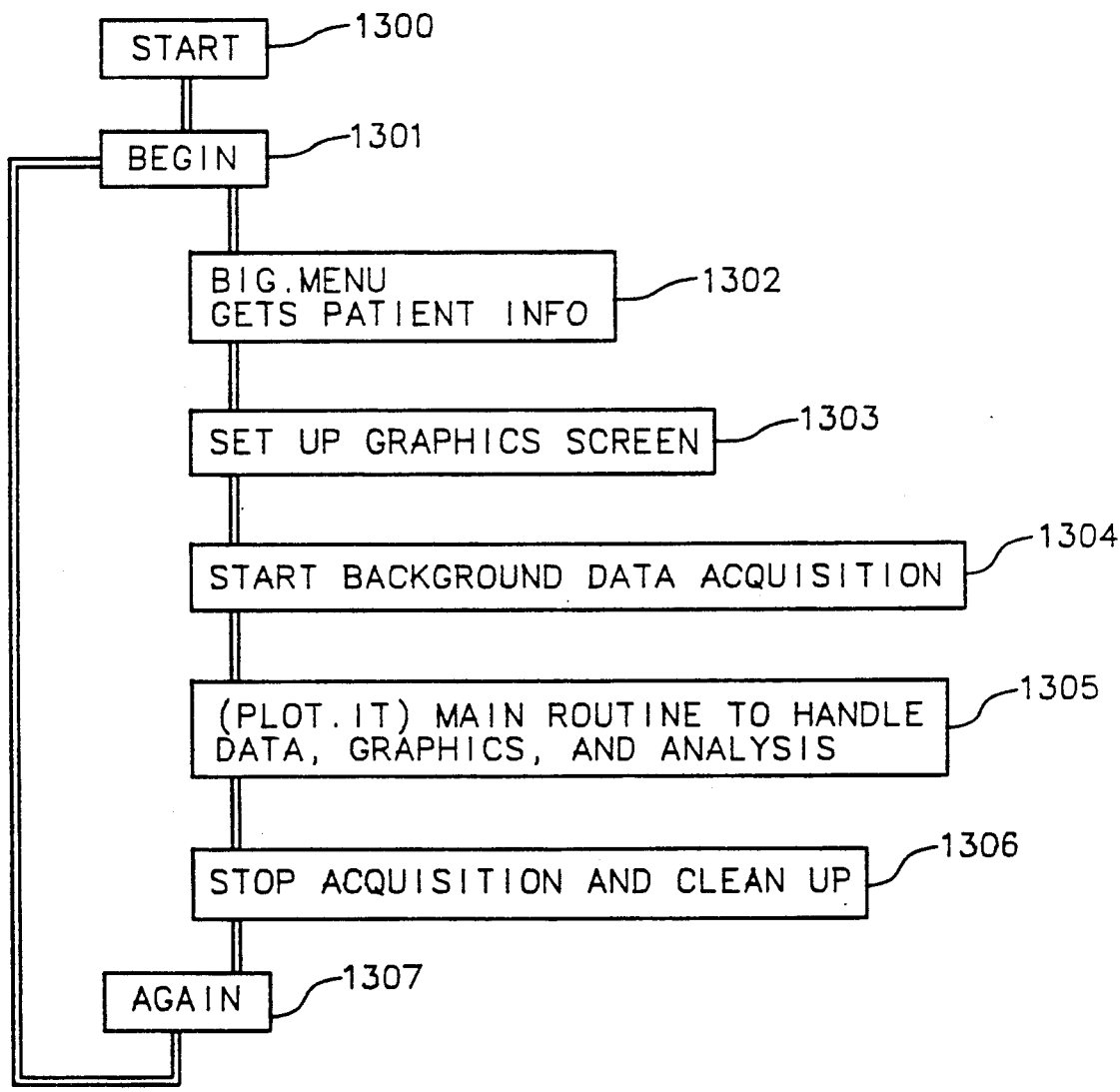
FIG. 13 is a flow chart of the computer program's primary loop.

FIGS. 13-19 illustrate flow charts of a program suitable for operation of central processing unit 6. FIG. 13 shows the primary loop program for central processing unit operation. Block 1300 initiates the operation of the program. Block 1301 repeats the primary loop upon a prompt from block 1307. Block 1302 instructs the operator to enter patient information such as name, sex, age and weight. The program screen graphics are controlled by block 1303. Background data acquisition is initiated by block 1304. Block 1305 is the main routine for data acquisition, graphics control and program analysis. Data acquisition is terminated at block 1306. Block 1307 loops the program to block 1301 above.

C. Data Acquisition and Analysis Control Program

Figure 14:
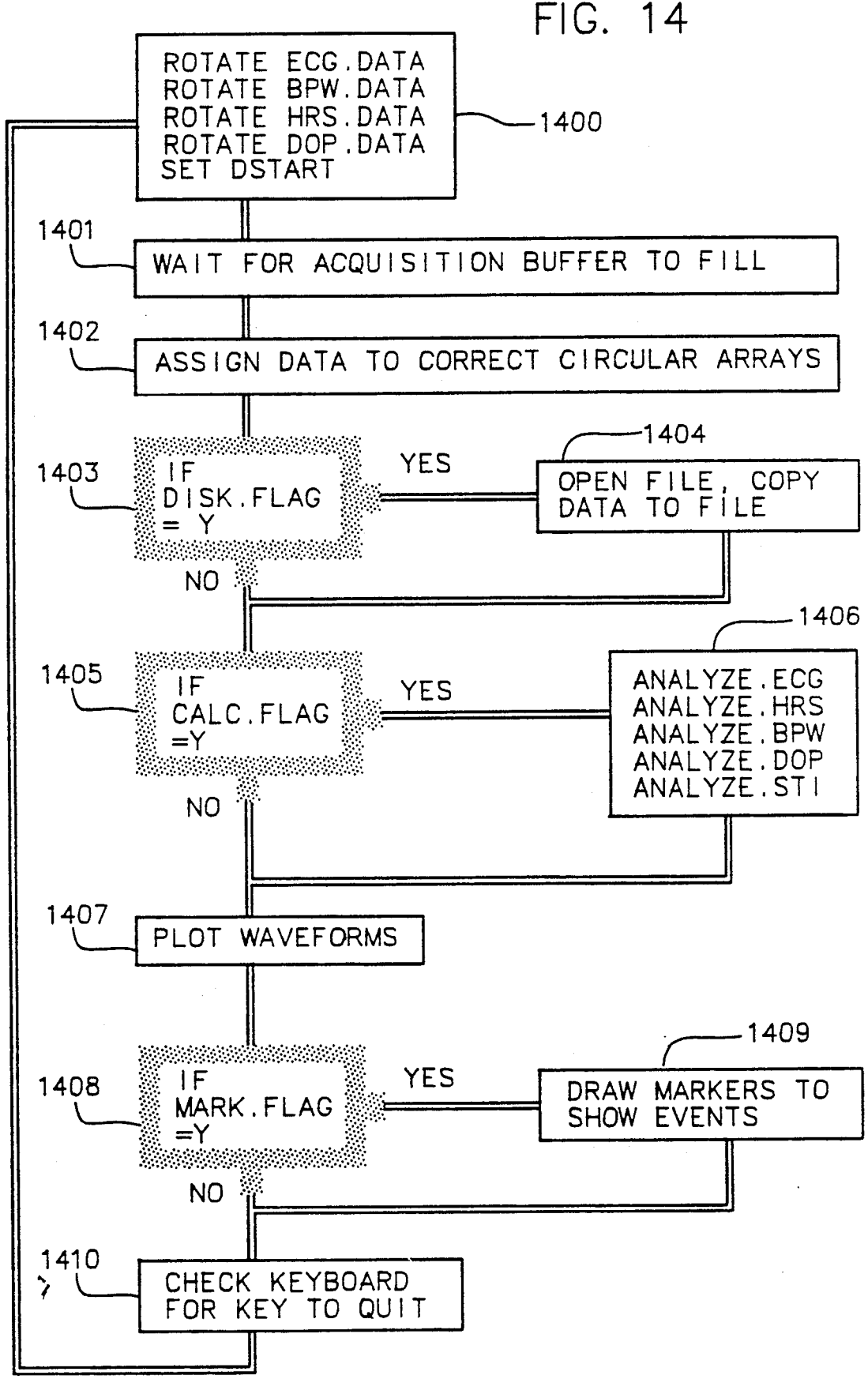
FIG. 14 is a flow chart of the computer program's main routine.

FIG. 14 shows a flow chart of the main program for the control of data acquisition and analysis. Block 1400 rotates by 180° the circular data arrays of the electrocardiogram waveform (ecg.data), volume oscillometric pulse wave form (bpw.data), phonocardiographic waveform (hrs.data), and multi-crystal piezoelectric doppler pulse waveform (dop.data) based on the scalar dstart which ascertains the last detected event. Block 1401 instructs the program to wait until the acquisition buffer is loaded with data. In block 1402, data acquired is assigned to the appropriate circular arrays as listed in block 1400. Block 1403 is a decision block for the disk.-flag activity option. If "yes" is chosen at block 1403, the program, at block 1404, opens a file and copies data to this file. The program then proceeds to block 1405 from block 1404. If "no" is chosen at block 1403, the program proceeds directly to block 1405.

Block 1405 is a decision block for the calc.flag activity option. If "yes" is selected at block 1405, the program, at block 1406, analyzes the electrocardiographic data (analyze.ecg), the phonocardiographic data (analyze.hrs), the volume oscillometric data (analyze.bpw), the multi-crystal piezoelectric doppler pulse wave data (analyze.dop), and the systolic time interval data (analyze.sti). The program then proceeds to block 1407 from block 1406. If "no" is chosen at block 1405, the program proceeds directly to block 1407.

Block 1407 directs the plotting of the waveforms based on the data received. Block 1408 is a decision block for the mark.flag activity option. If "yes" is chosen at block 1408, the program, at block 1409, draws markers to show the key data points for the cardiac initiation point (flag 1 of FIG. 20), the arterial pulse wave initiation point (flag 2 or 2' of FIG. 20), the high frequency component of the second heart sound (flag 3 of FIG. 20) and the dicrotic notch (flag 4 or 4' of FIG. 20). The program then proceeds to block 1410 from block 1409. If "no" is chosen at block 1408, the program proceeds directly to block 1410. Block 1410 loops the program back to block 1400 unless a quit key has been depressed on the keyboard.

D. Electrocardiographic Wave Analysis Program

Figure 15:
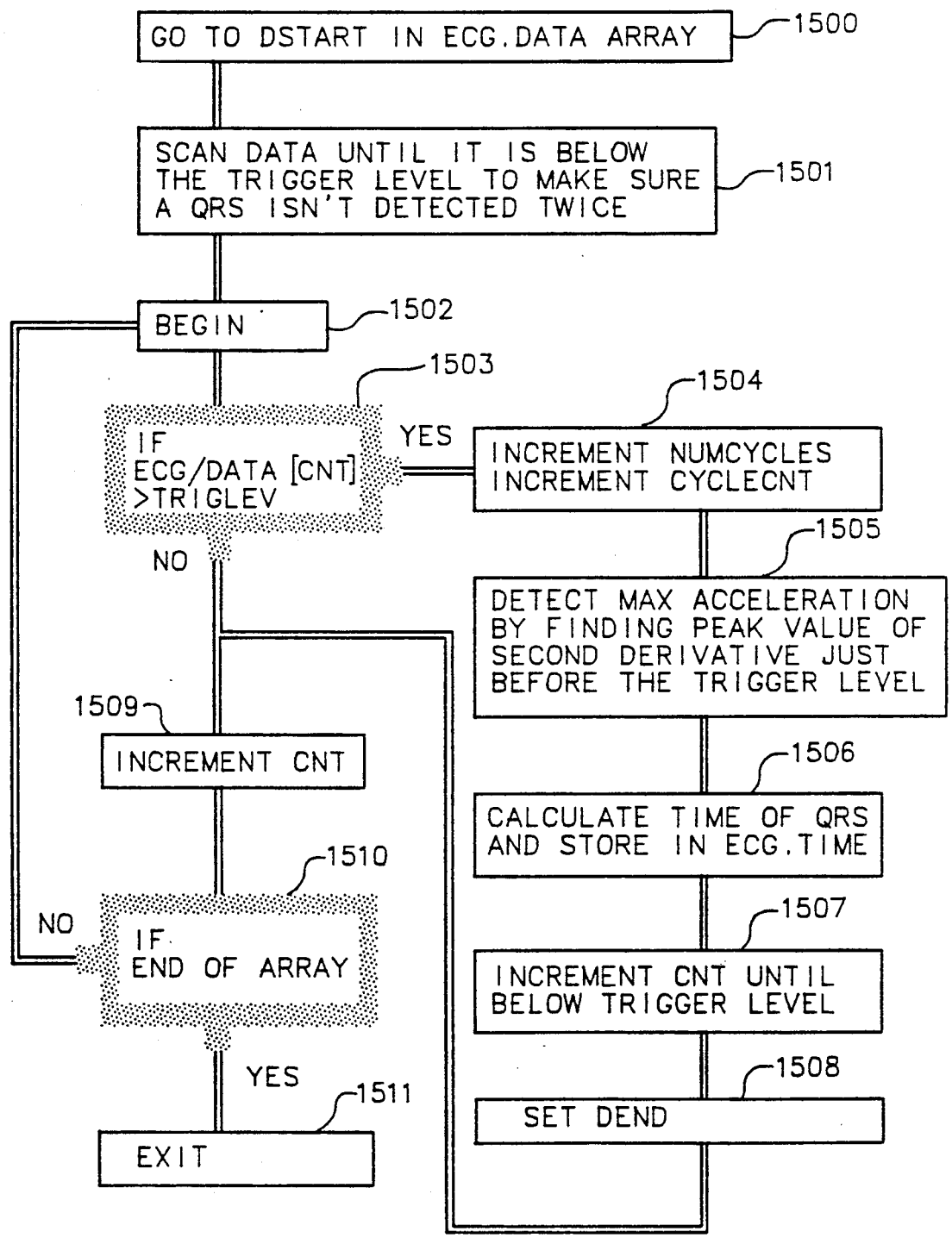
FIG. 15 is a flow chart of the electrocardiogram analyzing computer program.

FIG. 15 shows a flow chart for the program which analyzes the electrocardiographic wave data to determine the cardiac initiation point of the QRS wave, or electromechanical systole wave. The electrocardiographic wave is used as a reference for all other events because of its accuracy. Block 1500 instructs the program to go to the scalar dstart for the electrocardiographic data array, ecg.data, in order to ascertain the last detected data event. Based on block 1501, the program scans the data until the data is below a predetermined trigger level to insure that the QRS wave is not detected twice. Block 1502 initiates the actual program. Block 1503 is a decision block for the comparison of the electrocardiographic data (ecg.data) and the trigger level value (triglev). If the ecg.data is greater than the triglev, the program proceeds to block 1504 where the number of QRS waves detected in an event (nomcycles)

and the total number of QRS waves detected (cyclecnt) are incremented. Then, at block 1505, maximum acceleration is ascertained by locating the peak value of the second derivative just preceding the trigger level. At block 1506, the time of the QRS wave initiation is calculated and stored in ecg.time. Block 1507 increments the cnt (the position of the data array being analyzed) until it is below the trigger level. Block 1508 sets dend. The program then proceeds to block 1509 from block 1508.

If, however, the ecg.data is not greater than triglev, the program proceeds from block 1503 directly to block 1509 instead of first going to block 1504–block 1508. Block 1509 increments the cnt (the cnt holds the position of the array being analyzed). Block 1510 is a decision block for the end of the data array. If it is not the end of the data array, the program returns to block 1502. If it is the end of the data array, the program proceeds to exit block 1511.

E. Volume Oscillometric Wave Analysis Program

Figure 16:
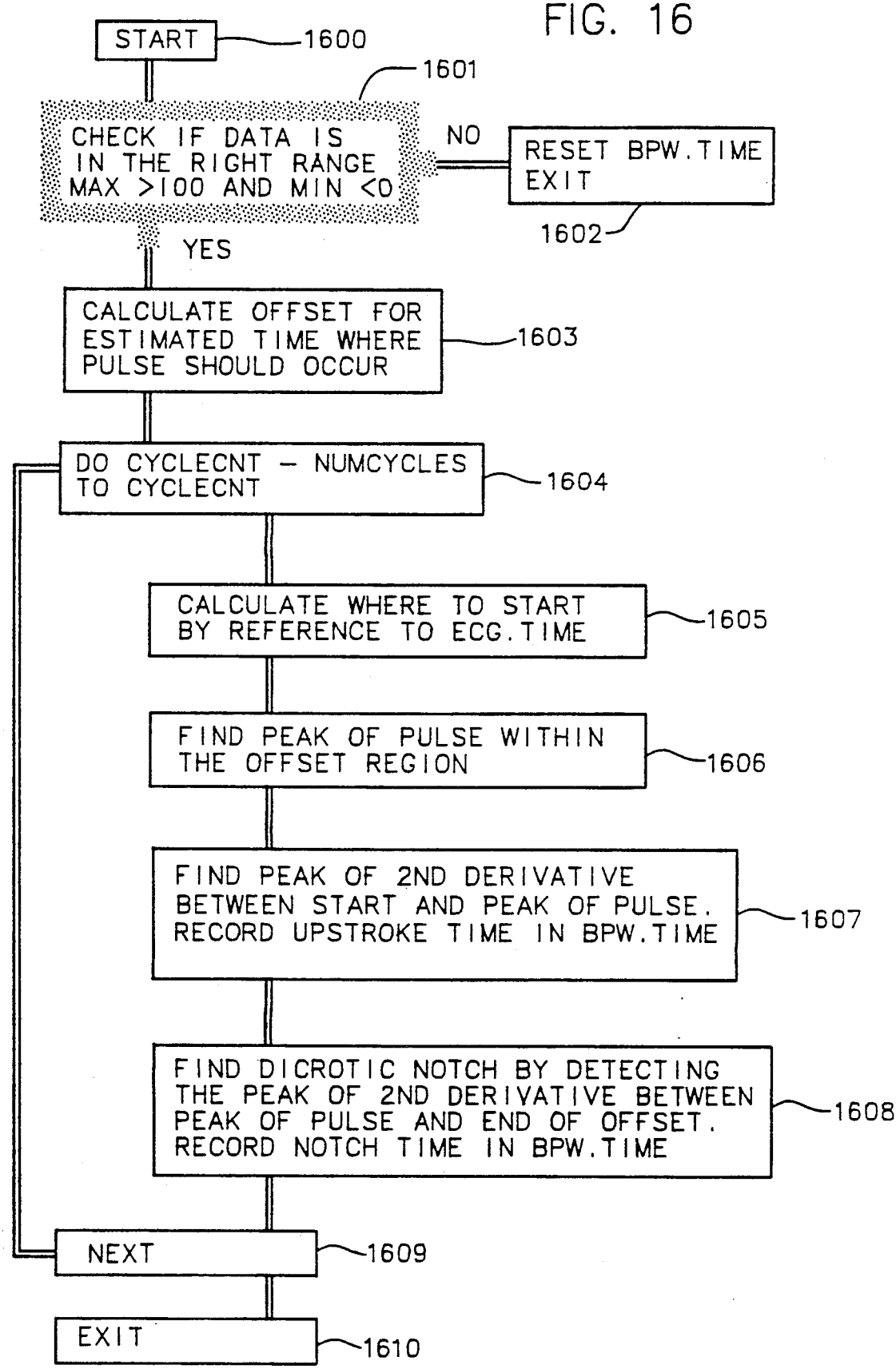
FIG. 16 is a flow chart of the volume oscillometric pulse wave analyzing computer program.

FIG. 16 shows a flow chart for the program which analyzes the volume oscillometric wave data to determine the arterial wave initiation point and the dicrotic notch. Block 1600 initiates the program. Decision block 1601 ascertains whether the program is greater than 100 or less than 0. If the data is not greater than 100 or less than 0, the program proceeds to block 1602 where the volume oscillometric wave time, or bpw.time, is reset. If the data is greater than 100 or less than 0, the program proceeds to block 1603 instead of block 1602. Block 1603 calculates an offset value based on an estimate of when the pulse should occur. The program then proceeds to block 1604 where limits are ascertained in which to record time values in arrays. At block 1604, the start position is derived based on the ecg.time. Block 1606 finds the pulse peak within the offset region. Block 1607 locates the peak of the second derivative between the pulse start point and pulse peak point. Block 1607 also records the pulse upstroke time based in bpw.time. At block 1608, the dicrotic notch is located by detecting the peak of the second derivative between the pulse peak point and the offset end point. Block 1608 also records the dicrotic notch time in bpw.time. Block 1609 either loops the program back to block 1604 or causes the program to exit through exit block 1610.

F. Phonocardiographic Wave Analysis Program

Figure 17:
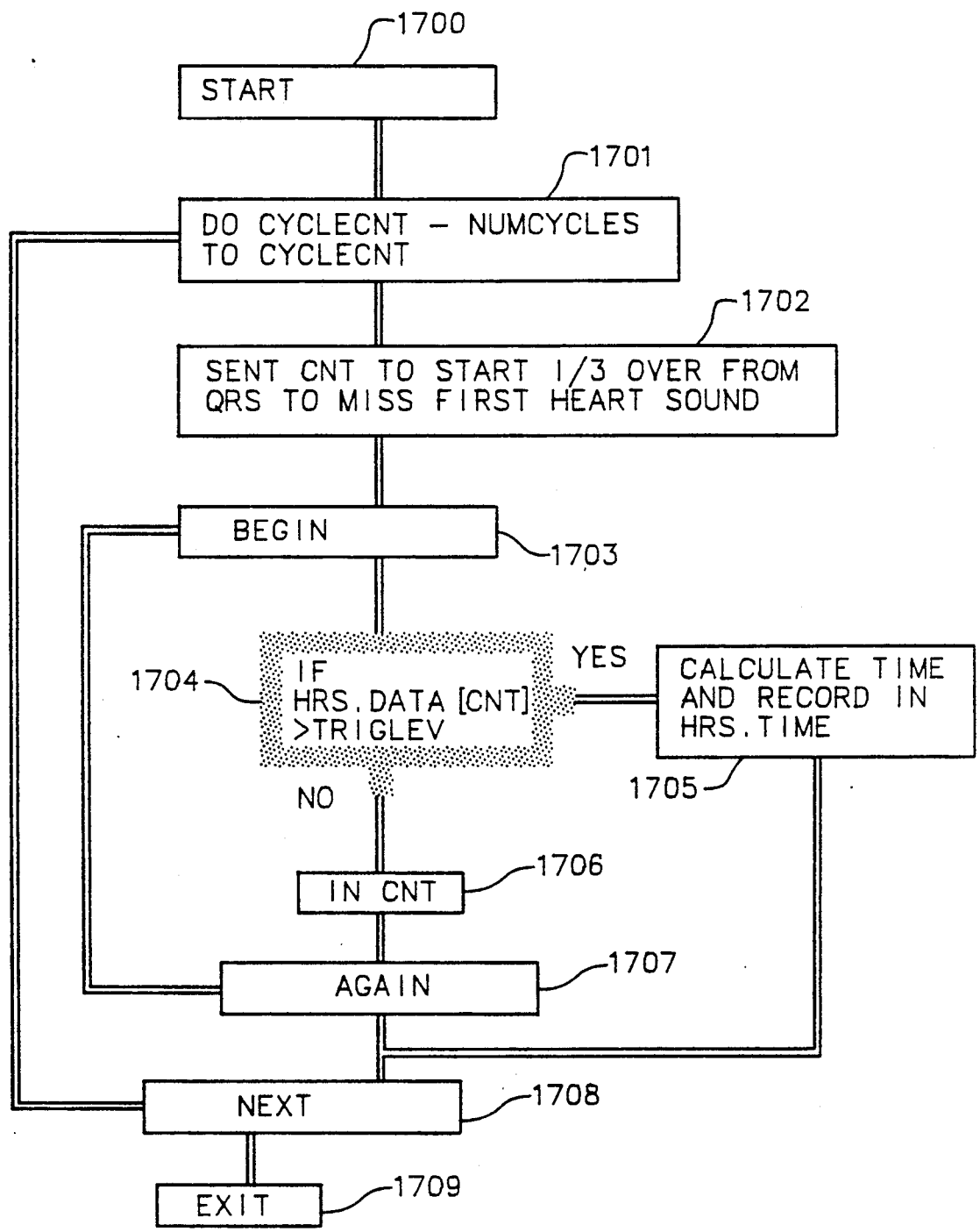
FIG. 17 is a flow chart of the phonocardiographic analyzing computer program.

FIG. 17 is a flow chart for the program which analyzes the phonocardiographic wave data to derive the high frequency component of the second heart sound. Block 1700 initiates the program. Block 1701 derives limits in which to record time values in arrays. Block 1702 sets cnt, the position of the data array being analyzed, to start ⅓ of the distance of the QRS wave in order to avoid analyzing the first heart sound. Block 1703 initiates the actual analysis by the program. Block 1704 is a decision block for the comparison of the phonographic data (hrs.data) and the predetermined trigger level value (triglev). If the hrs.data is greater than the triglev, the program proceeds to block 1705 which calculates the time value and records it in hrs.time. Block 1705 then leads to block 1708 described in detail below.

If, however, the hrs.data is not greater than triglev, the program proceeds from block 1704 to block 1706 instead of going to block 1705. Block 1706 increments the cnt (the cnt holds the position of the array being analyzed). Block 1707 either loops the program back to block 1703 or passes the program to next block 1708. At block 1708 the program either loops back to block 1701 or exits at exit block 1709.

G. Doppler Pulse Wave Analysis Program

Figure 18:
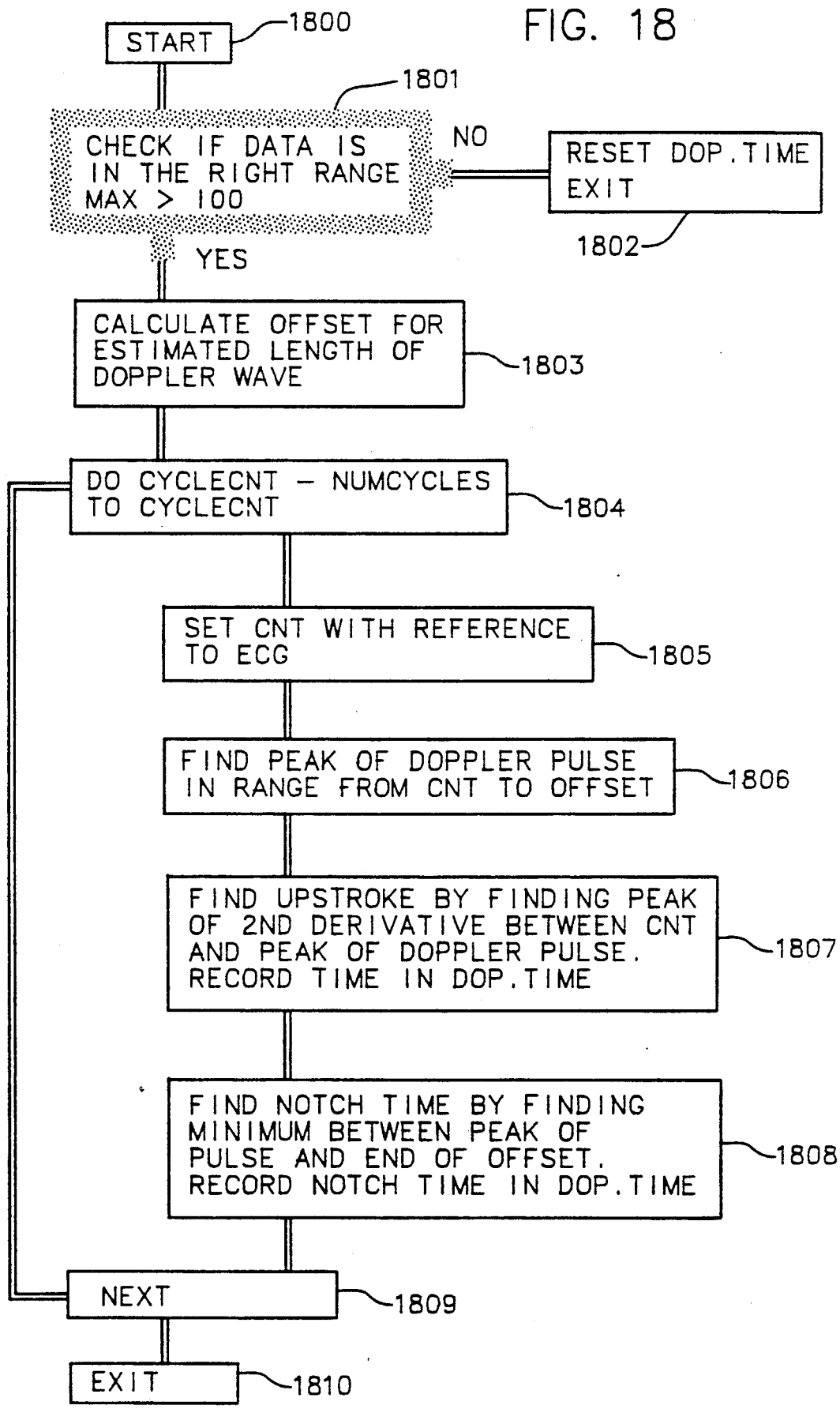
FIG. 18 is a flow chart of the multi-crystal piezoelectric doppler analyzing computer program.
Figure 19A:
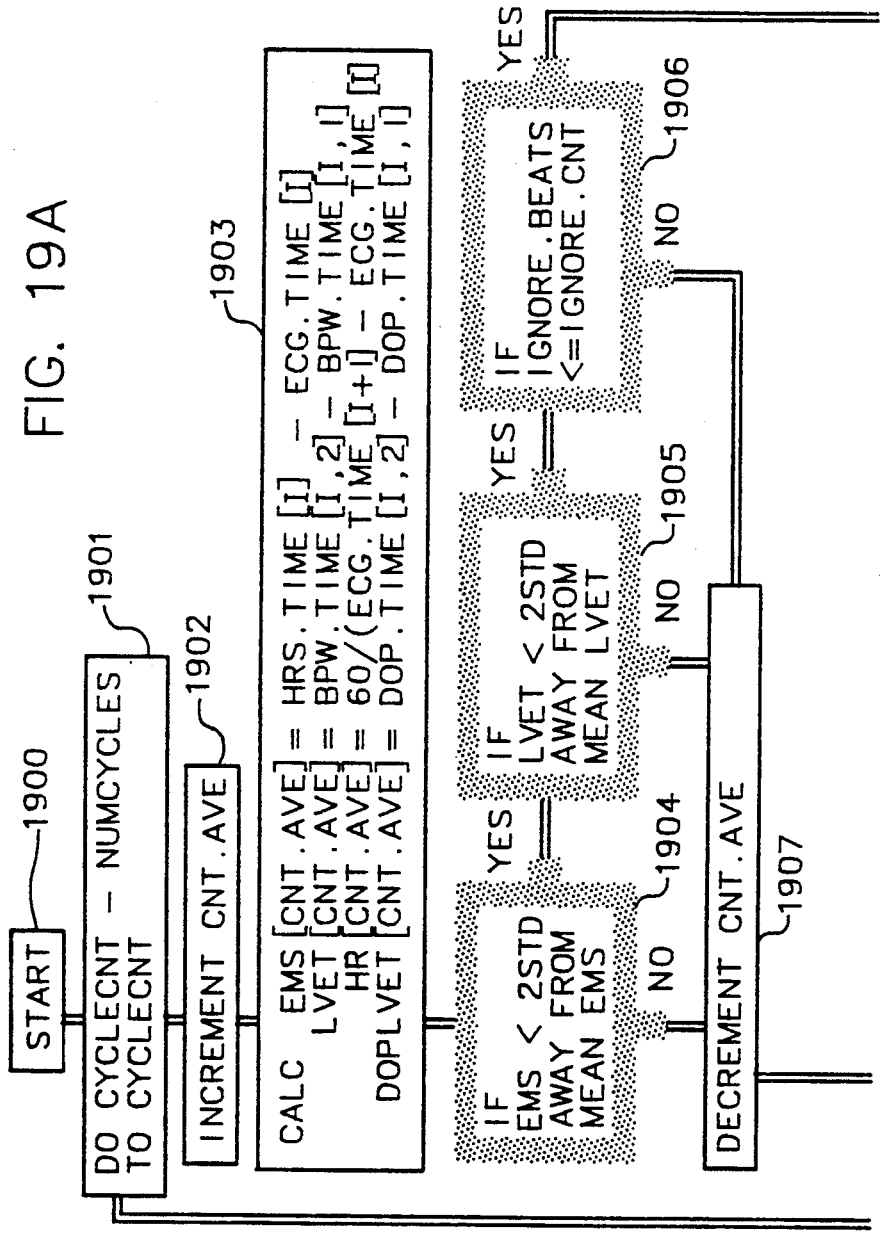

FIG. 18 is a flow chart for the program which analyzes the multi-crystal piezoelectric doppler pulse wave data to derive the arterial initiation points and the dicrotic notch. Block 1800 initiates the program. Decision block 1801 ascertains whether the program data has an appropriate value of over 100. If the data does not exceed 100, the program proceeds to block 1802 where the piezoelectric doppler pulse wave time, or dop.time, is reset. If the data is greater than 100, the program proceeds to block 1803 instead of block 1802. Block 1803 calculates an offset value based on an estimated doppler wave length. The program then proceeds to block 1804 where limits are set in which to record time values in arrays. At block 1805, the cnt, which holds the position of the array being analyzed, is set with reference to the electrocardiogram program data, above. Block 1806 then locates the doppler pulse peak in the range from the cnt value of block 1805 to the offset value of block 1803. Block 1807 ascertains the upstroke by finding the peak of the second derivative between the cnt and the doppler pulse peak. Block 1807 also records the upstroke time in dop.time. Block 1808 then finds the dicrotic notch by locating the minimum value between the pulse peak and the offset value. Block 1808 records the dicrotic notch time in dop.time. Block 1809 either loops the program back to block 1804 or causes the program to exit through exit block 1810.

H. EMS, LVET, STI and EF Analysis Program

Figure 19:
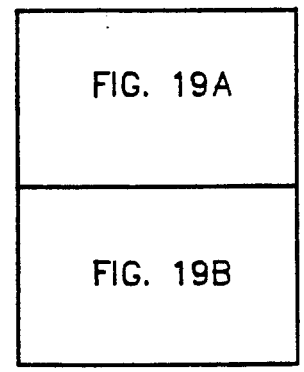

FIG. 19 represents a flow chart for the program which ascertains in real time the Electromechanical Systole, Left Ventricular Ejection Time, Systolic Time Interval and Ejection Fraction. Block 1901 derives limits in which to record time values in arrays. Blocks 1902 and 1903 calculate EMS, LVET, HR (heart rate), an DOPLVET (Doppler LVET) values. EMS is calculated by subtracting the ecg.time value from the HRS.time value (flag 1 from flag 3 in FIG. 20). LVET is calculated by subtracting the second bpw.time value from the first bpw.time value (flag 2 from flag 4 in FIG. 20). DOPLVET is calculated by subtracting the first dop.time value from the second dop.time value (flag 2' from flag 4' in FIG. 20).

Blocks 1904 and 1905 are decision blocks based on the standard deviation from mean values of EMS and LVET. If the calculated EMS value is within two standard deviations away from the mean EMS value then the program proceeds to block 1905.

In block 1905, if the LVET value is within two standard deviations from the mean LVET value then it proceeds to block 1906.

In block 1906, if a predefined number of beats have been skipped then it continues to block 1908.

If any of blocks 1904, 1905, or 1906 are answered in the negative, then the program skips block 1908 and proceeds to block 1907 which decrements a counter so that it ignores the last values calculated for EMS and LVET. The program then proceeds to block 1917 which is a NEXT statement. The program can loop to block 1901 or exit at block 1918.

Block 1908 is a decision block that controls how many values over which to average the values. The number of values averaged is set by the variable num.- to.cnt. This allows the user to change how many values are averaged. In block 1908, if the number of values counted equals the predefined number of values to average, the program proceeds to block 1909, otherwise it skips block 1909 and goes to block 1917 which is the NEXT statement.

Block 1909 calculates the average heart rate, EMS, LVET, and two standard deviations of mean EMS and mean LVET.

Block 1910 is a decision block based on patient sex. If the patient is a male, the program proceeds to block 1911 where $LVET_c$ and $EMS_c$ values are ascertained based on the formulas in block 1911.

If, however, the patient is female, the program proceeds from block 1910 to block 1912, not block 1911. $LVET_c$ and $EMS_c$ values are ascertained based on the formulas in block 1912.

After the program has derived $LVET_c$ and $EMS_c$ based on patient sex at either block 1911 or 1912, the program proceeds to decision block 1913. If the patient has Left Bundle Branch Block, the STI is derived based on the formula in block 1914. If the patient does not have LBBB, the program proceeds directly to block 1915 where the STI is derived. After the STI is ascertained at either block 1914 or 1915, the program ascertains the Ejection Fraction at block 1916.

After block 1916, the program loops to block 1901 via next block 1917 or exits at block 1918.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the spirit and scope of the invention.

I claim:

1. An apparatus for sensing cardiac performance comprising:
   a plurality of noninvasive sensors adapted to be attached to a patient for producing electrical analog sensor signals representing cardiac wave initiation points, high-frequency components of second heart sounds, arterial pulse wave initiation points, and arterial pulse wave dicrotic notches;
   means for processing said electrical analog signals to produce a signal representing systolic time intervals as a responsive function of said electrical analog sensor signals; and
   means for producing an electrical signal representing ejection fractions as a responsive function of said signal representing systolic time intervals.

2. The apparatus of claim 1, wherein said means for processing said electrical analog sensor signals comprises means for producing an electrical signal representing ejection fractions as a responsive function of said signal representing systolic time intervals.

3. The apparatus of claim 1, further comprising a signal display means for displaying graphic representations of at least certain of said electrical analog sensor signals from said noninvasive sensors and for displaying the level of said signal representing said ejection fractions.

4. The apparatus of claim 1, wherein said noninvasive sensors include a sensor for measuring arterial pulse wave doppler shifts comprising:
   sound wave generating means;
   sound wave receiving means;
   a sensor body for holding said sound wave generating means and sound wave receiving means in proximity to an artery of a patient; and
   signal conditioning and processing means for deriving a frequency shift in a sound wave transmitted by said sound wave generating means and received by said sound wave receiving means, the frequency shift being based on the velocity of blood cells within the artery.

5. The apparatus of claim 4, wherein said sound wave generating means comprises a plurality of electrical to sound transducers arranged on said sensor body in proximity to said sound wave receiving means.

6. The apparatus of claim 4, wherein said sound wave receiving means comprises a plurality of sound to electrical signal transducers arranged on said sensor body in proximity to said sound wave generating means.

7. The apparatus of claim 4, wherein said sound wave generating means comprises a plurality of transmit transducers arrayed along a transmit axis on said sensor body, and said sound wave receiving means comprises a plurality of sound to electrical signal transducers arrayed along a receive axis on said sensor body, said transmit axis and said receive axis being substantially parallel and separated so that at least certain transmit transducers and certain receive transducers are positioned relative to the patient's artery for deriving said frequency shift as a result of velocity of blood cells within the artery.

8. The apparatus of claim 4, wherein said signal conditioning and processing means comprises oscillator means and demodulator means, said oscillator means being coupled to said sound generating means and to said demodulator means for causing sound waves to be generated by said sound wave generating means, and to provide a transmit carrier signal to said demodulator means, said demodulator means also being coupled to said sound wave receiving means so that sound wave receiving signals are demodulated by said demodulator means relative to said transmit carrier signal to produce an output signal representing the frequency shift based on the velocity of blood cells within the artery.

9. The apparatus of claim 8, further comprising band pass filter means interposed between said sound wave receiving means and said demodulator means.

10. The apparatus of claim 8, further comprising a gain stage means coupled to an output of said demodulator means for producing an audio output signal representing the frequency shift based on the velocity of blood cells within the patient's artery.

11. The apparatus of claim 1, wherein said noninvasive sensors include a sensor for measuring cardiac sound waves comprising:
   a body having a first chamber and a second chamber, said first chamber and said second chamber being substantially sound isolated with respect to each other;
   a first sound sensor means in said first chamber for receiving patient cardiac sound waves and noise sound waves and for developing electrical signals based on the cardiac sound waves and noise sound waves;
   a second sound sensor means in said second chamber for receiving only noise sound waves and for developing electrical signals based on the noise sound waves; and
   signal conditioning and processing means for deriving a signal representing cardiac sound wave values based on the difference between said signals of said first sound sensor means and said signals of said second sound sensor means.

12. The apparatus of claim 11, wherein said cardiac sound wave sensor comprising:
   signal differencing circuit means having a first input coupled to said first sound sensor means and a second input coupled to said second sound sensor means and having an output at which difference signal is produced;
   adjustable gain means associated with said signal differencing circuit means for adjustably zeroing out a noise component in said difference signal;
   switchable frequency window filter means coupled to said output of said signal differencing circuit means; and
   variable output gain stage means coupled to said switchable frequency filter means, said variable output gain stage means having an output at which an audio signal is produced representing said cardiac sound waves.

13. The apparatus of claim 12, wherein said switchable frequency filter means comprises a binary switching means for controlling said filter means by a binary control signal.

14. The apparatus of claim 12 wherein said switchable frequency filter means comprises a switchable center frequency control means for selectively changing a center frequency of said filter means.

15. The apparatus of claim 12, further comprising a first input filter stage interposed between said first sound sensor means and said first input of said signal differencing circuit means, and a second input filter stage interposed between said second sound sensor means and second input of said signal differencing circuit means.

16. The apparatus of claim 1, wherein said noninvasive sensors include a sensor for measuring volume oscillometric pulse waves comprising:
   an inflatable cuff means for converting a patient's pulse waves into internal air pressure variations within said inflatable arm cuff means;
   a pump means for inflating said inflatable arm cuff means;
   an air line connecting said inflatable arm cuff means and said pump means;
   a valve means for regulating air flow of said inflatable arm cuff means;
   a pressure transducer means in said air line for converting said internal air pressure variations of said inflatable arm cuff means into electrical signals;
   signal conditioning and processing means for deriving volume oscillometric pulse wave values based on said internal air pressure variations of said inflatable arm cuff means.

17. The apparatus of claim 16, wherein said signal conditioning and processing means for deriving volume oscillometric pulse wave values comprises a first signal path having a first filter means that filters out fluctuations in the output of said pressure transducer means so as to produce a signal representing patient blood pressure; and
   a second signal path means comprising filter means for extracting variations in the output of said pressure transducer means so as to produce a fluctuating signal representing the patient's pulse wave, said second signal path comprising a differentiating means for differentiating a signal developed by said pressure transducer.

18. The apparatus of claim 17, wherein said second signal path comprises a low pass filter means coupled in said second signal path after said differentiating means.

19. An apparatus for sensing cardiac performance in substantially real time comprising:
   a noninvasive electrocardiographic sensor means adapted to be attached to a patient for producing electrical analog signals representing cardiac wave initiation points;
   a noninvasive phonocardiographic sensor means adapted to be attached to a patient for producing electrical analog signals representing high-frequency components of second heart sounds;
   a noninvasive arterial volumetric pulse wave sensor means adapted to be attached to a patient for producing electrical analog signals representing arterial pulse wave initiation points and representing arterial pulse wave dicrotic notches;
   a noninvasive arterial doppler pulse wave sensor means adapted to be attached to a patient for producing electrical analog signals representing arterial pulse wave initiation points and representing arterial pulse wave dicrotic notches;
   an analog-digital converter for converting said analog electrical signals from said electrocardiographic sensor means, said phonocardiographic sensor means, said arterial volumetric pulse wave sensor means and said arterial doppler pulse wave sensor means into digital signals as a function of time; and
   a means for processing said digital signals to derive average arterial pulse wave digital signals based on said digital signals representing said arterial pulse wave initiation points and said arterial pulse wave dicrotic notches received by said arterial volumetric pulse wave sensor means and by said arterial doppler pulse wave sensor means,
   a heart rate value based on said digital signals representing said cardiac wave initiation points,
   an electromechanical systole value based on said digital signals representing said cardiac wave initiation points and said high-frequency components of second heart sounds,
   a left ventricular ejection time value based on said average arterial pulse wave digital signals representing said arterial pulse wave initiation points and said arterial pulse wave dicrotic notches,
   a systolic time interval value based on said heart rate value, said electromechanical systole value and said left ventricular ejection time value, and
   an ejection fraction value based on said systolic time interval value.

20. The apparatus of claim 19, further comprising a signal display means for displaying in real time graphic representations of said electrical analog signals from said noninvasive electrocardiographic sensor means, said noninvasive phonocardiographic sensor means, said noninvasive arterial volumetric pulse wave sensor means and said noninvasive arterial doppler sensor means, and for displaying in real time said heart rate value, said electromechanical systole value, said left ventricular ejection time value, said ejection fraction value, and average values based on a plurality of said ejection fraction values.

21. The apparatus of claim 19, wherein said means for processing said digital signals derives said systolic time interval value based on the following formula:

$$STI = \frac{EMS_{corrected} - LVET_{corrected} + 0.4\ HR}{LVET_{corrected}}$$

where
$EMS_{corrected}$=EMS+2.0 HR where the patient is female;
$EMS_{corrected}$=EMS+2.1 HR where the patient is male;
$LVET_{corrected}$=LVET+1.6 HR where the patient is female;
$LVET_{corrected}$=LVET+1.7 HR where the patient is male; HR=said heart rate value;
EMS=said electromechanical systole value;
LVET=said left ventricular ejection time value.

22. The apparatus of claim 19, wherein said means for processing said digital signals derives said ejection fraction value based on the following formula:

EF=1.125−STI 1.25 where STI=said systolic time interval value.

23. The apparatus of claim 19, further comprising a noninvasive thermister sensor means adapted to be attached to a patient for producing electrical analog signals representing skin temperature.

24. The apparatus of claim 19, further comprising a noninvasive oximeter sensor means adapted to be attached to a patient for producing electrical analog signals representing blood oxygenation level.

25. An apparatus for real time sensing of cardiac performance comprising:
   a noninvasive electrocardiographic sensor means adapted to be attached to a patient for producing electrical analog signals representing cardiac wave initiation points;
   a noninvasive phonocardiographic sensor means adapted to be attached to a patient for producing electrical analog signals representing high-frequency components of second heart sounds;
   a noninvasive arterial volumetric pulse wave sensor means adapted to be attached to a patient for producing electrical analog signals representing arterial pulse wave initiation points and representing arterial pulse wave dicrotic notches;
   a noninvasive arterial doppler pulse wave sensor means adapted to be attached to a patient for producing electrical analog signals representing arterial pulse wave initiation points and representing arterial pulse wave dicrotic notches;
   an analog-digital converter for converting said analog electrical signals from said electrocardiographic sensor means, said phonocardiographic sensor means, said arterial volumetric pulse wave sensor means and said arterial doppler pulse wave sensor means into digital signals as a function of time;
   a means for processing said digital signals to derive heart rate values based on said digital signals representing said cardiac wave initiation points,
   a mean heart rate value based on a predetermined number of said heart rate values,
   electromechanical systole values based on said digital signals representing said cardiac wave initiation points and said high frequency components of second heart sounds,
   a mean electromechanical systole valve based on a predetermined number of electromechanical systole values,
   a refined electromechanical systole value based on a number of said electromechanical systole values within a predetermined numerical range from said mean electromechanical systole value,
   a corrected electromechanical systole value based on said refined electromechanical systole value and on patient sex,
   a left ventricular ejection time value based on said digital signals representing said arterial pulse wave initiation points and said arterial pulse wave dicrotic notches converted from said analog signals, said digital signals received by at least one of said arterial volumetric pulse wave sensor means and said arterial doppler pulse wave sensor means,
   a mean left ventricular ejection time valve based on a predetermined number of said left ventricular ejection time values,
   a refined left ventricular ejection time value based on a number of said left ventricular ejection time values within a predetermined numerical range from said mean left ventricular ejection time value;
   a corrected left ventricular ejection time value based on said refined left ventricular ejection time value and on patient sex,
   a systolic time interval value based on said mean heart rate value, said corrected electromechanical systole value and said corrected left ventricular ejection time value, and
   an ejection fraction value based on said systolic time interval value; and
   a signal display means for displaying in real time graphic representations of said electrical analog signals from said noninvasive electrocardiographic sensor means, said noninvasive phonocardiographic sensor means, said noninvasive arterial volumetric pulse wave sensor means and said noninvasive arterial doppler sensor means and for displaying in real time said heart rate values, said corrected electromechanical systole value, said corrected left ventricular ejection time value, said ejection fraction value, and average ejection fraction values based on a plurality of said ejection fraction values.

26. A noninvasive sensor for measuring arterial pulse wave doppler shifts comprising:
   a plurality of sound wave generating means;
   a plurality of sound wave receiving means;
   a sensor body for holding said sound wave generating means in proximity to an artery of a patient; and
   signal conditioning and processing means for deriving a frequency shift in a sound wave transmitted by at least one of said sound wave generating means and received by at least one of said sound wave receiving means, the frequency shift based on the velocity of blood cells within the artery.

27. The apparatus of claim 26, wherein said plurality of sound wave generating means comprises a plurality of electrical to sound transducers arranged on said sensor body in proximity to said plurality of sound wave receiving means.

28. The apparatus of claim 26, wherein said plurality of sound wave receiving means comprises a plurality of sound to electrical signal transducers arranged on said sensor body in proximity to said plurality of sound wave generating means.

29. The apparatus of claim 26, wherein said plurality of sound wave generating means comprises a plurality of transmit transducers arrayed along a transmit axis on said sensor body, and said plurality of sound wave receiving means comprises a plurality of sound to electrical signal transducers arrayed along a receive axis on said sensor body, said transmit axis and said receive axis being substantially parallel and separated so that at least certain transmit transducers and certain receive transducers are positioned relative to the patient's artery for deriving said frequency shift as a result of velocity of blood cells within the artery.

30. The apparatus of claim 26, wherein said signal conditioning and processing means comprises oscillator means and demodulator means, said oscillator means being coupled to said plurality of sound generating means and to said demodulator means for causing sound waves to be generated by said sound wave generating means, and to provide a transmit carrier signal to said demodulator means, said demodulator means also being coupled to said plurality of sound wave receiving means so that sound wave receiving signals are demodulated by said demodulator means relative to said transmit carrier signal to produce an output signal representing the frequency shift based on the velocity of blood cells within the artery.

31. The apparatus of claim 30, further comprising band pass filter means interposed between said plurality of sound wave receiving means and said demodulator means.

32. The apparatus of claim 31, further comprising a gain stage means coupled to an output of said demodulator means for producing an audio output signal representing the frequency shift based on the velocity of blood cells within the patient's artery.

33. An apparatus for sensing cardiac performance comprising:
   a plurality of non-invasive sensors adapted to be attached to a patient for producing electrical analog sensor signals representing cardiac wave initiation points, high-frequency components of second heart sounds, arterial pulse wave initiation points, and arterial pulse wave dicrotic notches;
   means for processing said electrical analog signals to produce a signal representing systolic time intervals as a responsive function of said electrical analog sensor signals including means for producing an electrical signal representing ejection fractions as a responsive function of said systolic time intervals; and
   signal display means for displaying graphic representations of at least certain of said electrical analog sensor signals from said non-invasive sensors and for displaying the level of said signal representing said ejection fractions.

34. An apparatus for sensing cardiac performance comprising:
   a plurality of non-invasive sensor adapted to be attached to a patient for producing electrical analog sensor signals representing cardiac wave initiation points, high-frequency components of second heart sounds, arterial pulse wave initiation points, and arterial pulse wave dicrotic notches;
   means for processing said electrical analog signals to produce a signal representing systolic time intervals as a responsive function of said electrical analog sensor signals;
   wherein said non-invasive sensors include a sensor for measuring arterial pulse wave doppler shifts comprising:
      sound wave generating means;
      sound wave receiving means;
      a sensor body for holding said sound wave generating means and sound wave receiving means is proximity to an artery of a patient; and
      signal conditioning and processing means for deriving a frequency shift in a sound wave transmitted by said sound wave generating means and received by said sound wave receiving means, the frequency shift being based on the velocity of blood cells within the artery; said signal conditioning and processing means comprises oscillator means and demodulator means, said oscillator means being coupled to said sound generating means and to said demodulator means for causing sound waves to be generated by said sound wave generating means, and to provide a transmit carrier signal to said demodulator means, said demodulator means also being coupled to said sound wave receiving means so that sound wave receiving signals are demodulated by said demodulator means relative to said transmit carrier signals to produce an output signal representing the frequency shift based on the velocity of blood cells within the artery.

35. An apparatus for sensing cardiac performance comprising:
   a plurality of non-invasive sensors adapted to be attached to a patient for producing electrical analog sensor signals representing cardiac wave initiation points, high-frequency cardiac wave initiation points, high-frequency components of second heart sounds, arterial pulse wave initiation points, and arterial pulse wave dicrotic notches;
   means for processing said electrical analog signals to produce a signal representing systolic time intervals as a responsive function of said electrical analog sensor signals;
   wherein said non-invasive sensors include a sensor for measuring volume oscillometric pulse waves comprising: p2 an inflatable cuff means for converting a patient's pulse waves into internal air pressure variations within said inflatable arm cuff means;
   a pump means for inflating said inflatable arm cuff means;
   an air line connecting said inflatable arm cuff means and said pump means;
   a valve means for regulating air flow of said inflatable arm cuff means;
   a pressure transducer means in said air line for converting said internal air pressure variations of said inflatable arm cuff means into electrical signals;
   signal conditioning and processing means for deriving volume oscillometric pulse wave values based on said internal air pressure variations of said inflatable arm cuff means.

36. A non-invasive sensor for measuring arterial pulse wave doppler shifts comprising:
   a plurality of sound wave generating means;
   a plurality of sound wave receiving means;
   a sensor body for holding said sound wave generating means in proximity to an artery of a patient;

signal conditioning and processing means for deriving a frequency shift in a sound wave transmitted by at least one of said sound wave generating means and received by at least one of said sound wave receiving means, the frequency shift based on the velocity of blood cells within the artery;

wherein said plurality of sound wave generating means comprises a plurality of electrical to sound transducers arranged on said sensor body in proximity to said plurality of sound wave receiving means.

37. A non-invasive sensor for measuring arterial pulse wave doppler shifts comprising:

a plurality of sound wave generating means;

a plurality of sound wave receiving means;

a sensor body for holding said sound wave generating means in proximity to an artery of a patient; and signal conditioning and processing means for deriving a frequency shift in a sound wave transmitted by at least one of said sound wave generating means and received by at least one of said sound wave receiving means, the frequency shift based on the velocity of blood cells within the artery;

wherein said plurality of sound wave receiving means comprise a plurality of sound to electrical signal transducers arranged on said sensor body in proximity to said plurality of sound wave generating means.

38. A non-invasive sensor for measuring arterial pulse wave doppler shifts comprising:

a plurality of sound wave generating means;

a plurality of sound wave receiving means;

a sensor body for holding said sound wave generating means in proximity to an artery of a patient; and signal conditioning and processing means for deriving a frequency shift in a sound wave transmitted by at least one of said sound wave generating means and received by at least one of said sound wave receiving means, the frequency shift based on the velocity of blood cells within the artery; and wherein said plurality of sound wave generating means comprise a plurality of transmit transducers arrayed along a transmit axis on said sensor body, said plurality of sound wave receiving means comprise a plurality of sound to electrical signal transducers arrayed along a receive axis on said sensor body, said transmit axis and said receive axis being substantially parallel and separated so that at least certain transmit transducers and certain receive transducers are positioned relative to the patient's artery for deriving said frequency shift as a result of velocity of blood cells within the artery.

39. A non-invasive sensor for measuring arterial pulse wave doppler shifts comprising:

a plurality of sound wave generating means;

a plurality of sound wave receiving means;

a sensor body for holding said sound wave generating means in proximity to an artery of a patient; and signal conditioning and processing means for deriving a frequency shift in a sound wave transmitted by at least one of said sound wave generating means and received by at least one of said sound wave receiving means, the frequency shift based on the velocity of blood cells within the artery, wherein said signal conditioning and processing means comprises oscillator means and demodulator means, said oscillator means being coupled to said plurality of sound generating means and to said demodulator means for causing sound waves to be generated by said sound wave generating means, and to provide a transmit carrier signal to said demodulator means, said demodulator means also being coupled to said plurality of sound wave receiving means so that sound wave receiving signals are demodulated by said demodulator means relative to said transmit carrier signal to produce an output signal representing the frequency shift based on the velocity of blood cells within the artery.

* * * * *